United States Patent [19]
Flickinger et al.

[11] Patent Number: 6,036,861
[45] Date of Patent: Mar. 14, 2000

[54] PROTEIN ADSORPTION BY VERY DENSE POROUS ZIRCONIUM OXIDE PARTICLES IN EXPANDED BEDS

[75] Inventors: Michael C. Flickinger, St. Paul; Michael J. Robichaud; John E. Morris, both of Minneapolis; Colleen M. Griffith, St. Paul, all of Minn.; Michael J. Annen, Monroeville, Pa.; Peter W. Carr, Minneapolis; Christopher Dunlap, St. Paul, both of Minn.

[73] Assignee: Regents of the University of Minnesota

[21] Appl. No.: 09/130,003

[22] Filed: Aug. 6, 1998

Related U.S. Application Data

[63] Continuation of application No. 08/394,714, Feb. 27, 1995, Pat. No. 5,837,826.

[51] Int. Cl.⁷ .................................................. B01D 15/00
[52] U.S. Cl. ........................ 210/263; 210/650; 210/661; 210/670; 210/691; 210/905; 210/502.1
[58] Field of Search .................................. 210/263, 650, 210/661, 670, 691, 905, 502.1

[56] References Cited

U.S. PATENT DOCUMENTS

| | | | |
|---|---|---|---|
| 3,782,075 | 1/1974 | Kirkland | 55/67 |
| 3,850,751 | 11/1974 | Messing | 195/63 |
| 3,855,172 | 12/1974 | Iler et al. | 260/39 R |
| 3,892,580 | 7/1975 | Messing | 106/41 |
| 3,910,851 | 10/1975 | Messing | 252/455 R |
| 3,956,179 | 5/1976 | Sebastian et al. | 252/430 |
| 4,010,242 | 3/1977 | Iler et al. | 423/335 |
| 4,067,689 | 1/1978 | Perrier et al. | 8/129 |
| 4,115,198 | 9/1978 | Coughlin et al. | 195/63 |
| 4,138,336 | 2/1979 | Mendel et al. | 210/198 C |
| 4,141,857 | 2/1979 | Levy et al. | 252/430 |
| 4,389,385 | 6/1983 | Ramsay | 423/338 |
| 4,589,927 | 5/1986 | Allen et al. | 134/25.1 |
| 4,675,113 | 6/1987 | Graves et al. | 210/635 |
| 5,015,373 | 5/1991 | Carr et al. | 210/198.2 |
| 5,055,194 | 10/1991 | Goetz et al. | 210/635 |
| 5,084,169 | 1/1992 | Noble et al. | 210/222 |
| 5,084,184 | 1/1992 | Burns | 210/656 |
| 5,108,597 | 4/1992 | Funkenbusch et al. | 210/198.2 |
| 5,110,624 | 5/1992 | Noble et al. | 427/212 |
| 5,114,577 | 5/1992 | Kusano et al. | 210/198.2 |
| 5,128,291 | 7/1992 | Wax et al. | 502/8 |
| 5,141,634 | 8/1992 | Carr et al. | 210/198.2 |
| 5,167,811 | 12/1992 | Graves et al. | 210/198.2 |
| 5,167,812 | 12/1992 | Graves et al. | 210/198.2 |
| 5,182,016 | 1/1993 | Funkenbusch et al. | 210/198.2 |
| 5,205,929 | 4/1993 | Carr et al. | 210/198.2 |
| 5,254,262 | 10/1993 | Funkenbusch et al. | 210/656 |
| 5,271,833 | 12/1993 | Funkenbusch et al. | 210/198.2 |
| 5,346,619 | 9/1994 | Funkenbusch et al. | 210/198.2 |
| 5,540,834 | 7/1996 | Carr et al. | 210/198.2 |

FOREIGN PATENT DOCUMENTS

| | | |
|---|---|---|
| 0 162 716 | 11/1985 | European Pat. Off. . |
| 0 331 283 | 9/1989 | European Pat. Off. . |
| 0 490 226 A1 | 6/1992 | European Pat. Off. . |
| WO 95/04012 | 9/1995 | WIPO . |

OTHER PUBLICATIONS

M. Annen et al., "The Preparation of Porous Zirconia by Continuous Flow and Batch Processes", *Abstracts of Papers*, Fine Paticle Society Meeting, Aug. 23–28 (1993) (Abstract Only).

M. Annen et al., "The Controlled Aggregation of Zirconia Colloids in the Presence of Urea–Formaldehyde Resins: Effect of the Rates of Polymerization and Polymer Adsorption on Secondary Particle Formation", *Abstracts of Papers*, AICHE Meeting, Nov. 7–12 (1993) (Abstract Only).

M. Annen et al., "The Controlled Aggregation of Colloids for the Preparation of Spherical, Porous Zirconia", *Abstracts of Papers*, AICHE Meeting, Nov. 7–12 (1993) (Abstract Only).

M. Annen et al., "Synthesis and Characterization of Porous Zirconia Supports for HPLC and Perfusion Chromatography", *Abstracts of Papers*, The Pittsburgh Conference, Abstract No. 900, Feb. 27–Mar. 4 (1994) (Abstract Only).

M. J. Annen et al., "Development of Porous Zirconia Spheres By Polymerization–Induced Colloid Aggregation—Effect of Polymerization Rate", *J. of Mat. Sci.*, 29, 6123–6130 (1994).

U. Bien–Vogelsang et al., "Synthesis of Stationary Phases for Reversed–Phase LC Using Silanization and Polymer Coating", *Chromatographia*, 19, 170–176 (1984).

J.A. Blackwell et al., "Ligand Exchange Chromatography of Free Amino Acids on Phosphated Zirconium Oxide Supports", *J. Liq. Chrom.*, 15, 727–751 (1992).

J.A. Blackwell et al., "Ligand Exchange Chromatography of Free Amino Acids and Proteins on Porous Microparticulate Zirconium Oxide", *J. Liq. Chrom.*, 15, 1487–1506 (1992).

J.A. Blackwell et al., "Ion–and Ligand–Exchange Chromatography of Proteins Using Porous Zirconium Oxide Supports in Organic and Inorganic Lewis Base Eluents", *J. Chromatogr.*, 596, 27–41 (1992).

J.A. Blackwell et al., "Fluoride–Modified Zirconium Oxide as a Biocompatible Stationary Phase for High–Performance Liquid Chromatography", *J. Chromatogr.*, 549, 59–75 (1992).

(List continued on next page.)

*Primary Examiner*—Michael P. Woodward
*Assistant Examiner*—C. Delacroix-Muirheid
*Attorney, Agent, or Firm*—Mueting, Raasch & Gebhardt, P.A.

[57] ABSTRACT

Porous Zirconia particles of specific gravity of 2.5–3.5 g/cm³ and mean particle sizes of 30–400 μm can be synthesized using oil emulsion methods from colloids and used for protein adsorption in stable expanded beds. Expanded beds of less than 1.0 settled bed height to diameter (approximately 10 ml bed volume) are stable at linear fluid velocities of at least about 100 cm/hour.

13 Claims, 10 Drawing Sheets

OTHER PUBLICATIONS

P. Carr et al., "Zirconium Oxide Based Supports for Biochromatographic Applications", *Chromatography in Biotechnology*, 529, Chapter 11, 147–164 (1993).

P. Carr, "Base Stable and Composite ZrO$_2$ Ceramic Supports for HPLC", *NSF Grant No.* CHE–9107029, Abstract, Dec. 1990.

P. Carr et al, "Base Stable and Composit Supports for HPLC", *NIH Grant submission*, Abstract, Nov. 1993.

P. Carr, "Base Stable and Composite Ceramic Supports for HPLC and Fluidized Bed Separation", *NIH Grant No.* GM45988, Abstract, Jun. 1990.

H. A. Chase, "Purification of Proteins by Adsorption Chromatography in Expanded Beds", *TIBTECH*, 12, 296–303 (1994).

H. A. Chase et al., "Affinity Purification of Proteins Using Expanded Beds", *J. Chromatogr.*, 597, 129–145 (1992).

S. M. Cramer et al., "Preparative Chromatography in Biotechnology", *Biotechnology*, 4, 217–225 (1993).

N. M. Draeger et al., "Liquid Fluidized Bed for Protein Purification", *Trans IChemE*, 69, Part C, 34–53 (1991).

N. M. Draeger et al., "Protein Adsorption in Liquid Fluidized Beds", *I.CHEM.E. Symposium Series, No. 18*, 160–173 (1990).

N. M. Draeger et al., "Liquid Fluidized Bed Adsorption of Protein in the Presence of Cells", *Bioseparation*, 2, 67–80 (1991).

N. M. Draeger et al., "Modelling of Protein Adsorption in Liquid Fluidized Beds", *Separations for Biotechnology 2*, 325–335 (1990).

C.J. Dunlap et al., "Dextran Coated Zirconia–A Stable Biocompatible Stationary Phase for HPLC", *Abstracts of Papers*, The Pittsburgh Conference, Abstract No. 518P, Feb. 27–Mar. 4 (1994) (Abstract Only).

M. C. Flickinger et al., "Cleanable Zirconia–Based Chromatographic Supports", Abstract Only, Keystone Bioseparations Meeting (1993).

M.C. Flickinger et al., "Use of Zirconia Supports for Fluidized–Bed Separations of Proteins", *Abstracts of Papers*, The Pittsburgh Conference, Abstract No. 899, Feb. 27–Mar. 4 (1994) (Abstract and Poster).

Ann–Kristin Barnfield Frej et al., "Recovery of a Recombinant Protein from an E. coli Homogenate Using Expanded Bed Absorption", Pharmacia BioProcess Technology AB, Uppsala, Sweden (Company Brochure). Available prior to Feb. 27, 1995.

Ann–Kristin Barnfield Frej et al., "Expanded Bed Adsorption — The Influence of Feedstock Properties on Performance", Pharmacia BioProcess Technology AB, Uppsala, Sweden (Company Brochure). Available prior to Feb. 27, 1995.

N.B. Gibson et al., "Cellulose Composites in Fluidised Bed Adsorption. Design and Application of Selective Solid Phases", *Cellulosics: Materials for Selective Separations and Other Technologies*, Chapter 7, pp. 55–62, Ellis Harwood, NY (1993).

G. R. Gilchrist et al., "Solid Phases for Protein Adsorption in Liquid Fluidized Beds: Comparison of Commercial and Custom–assembled Particles", *Separations for Biotechnology 3* 186–192 (1994).

M. Glavanovich et al., "Zirconia: An Easily Regenerable Chromatographic Support with Applications to Affinity Chromatography", *Abstracts of Papers*, 14th Minnesota Chromatography Forum, Abstract No. 18, May 4–6 (1992) (Abstract Only).

M. Glavanovich et al., "Easily Regenerable Affinity Chromatographic Zirconia–Based Support with Concanavalin A as a Model Ligand", *Anal. Chem.*, 66, 2584–2589 (1994).

D. J. Graves et al., "Bioseparations in the Magnetically Stabilized Fluidized Bed", Chapter 9, 187–207 Barker and Ganetsos, Eds., *Preparative and Production Scale Chromatography*, Marcel Dekker, Inc., NY (1993).

M. Hansson et al., "Single–Step Recovery of a Secreted Recombinant Protein by Expanded Bed Adsoprtion", *Bio/Technology*, 12, 285–288 (1994).

Harris et al., Protein purification methods –a practical approach, Oxford: IRL Press, 259–260 (1989).

P. Hedman et al., "Adapting Chromatography for Initial Large–Scale Protein Recovery", *ACS*, 271–274 (1992).

J. Howard et al., "Biotechnology Firms Set Sights on Improving Methods of Protein Purification", *Genetic Engineering News*, 8–9 (1994).

R.K. Iler, "Coacervates of Polyvinyl Alcohol and Colloidal Silica," *J. Colloid Interface Sci.*, 51, 388–393 (1975).

S. Johansson et al., "Scale–up Validation of Expanded Bed Adsorption Processes", Pharmcia BioProcess Technology Company Brochure, Uppsala, Sweden. Available prior to Feb. 27, 1995.

S. Kämpe et al., "Charaterization of a Novel Adsorbent for Recovery of Proteins in Expanded Beds", Pharmacia BioProcess Technology (Company Brochure), Uppsala, Sweden. Available prior to Feb. 27, 1995.

B.J. Kellett et al., "Thermodynamics of Densification: I, Sintering of Simple Particle Arrays, Equilibrium Configurations, Pore Stability, and Shrinkage," *J. Amer. Ceram. Soc.*, 72(5), 725–734 (1989).

J. F. Kennedy et al., "Microbial Cells Living Immobilised on Metal Hydroxides", *Nature*, 261, 242–244 (1976).

P. Kolla et al., "Polymer–Coated Cation–Exchange Stationary Phases on the Basis of Silica", *Chromatographia*, 23(7), 465–472 (1987).

F. F. Lange, "Powder Processing Science and Technology for Increased Reliablity", *J. Am. Ceram. Soc.*, 72(1) 3–15 (1989).

F.F. Lange, "Thermodynamics of Densification: II, Grain Growth in Porous Compacts and Relation to Densification," *J. Amer. Ceram. Soc.*, 72(5), 735–741 (1989).

C. H. Lochmüller et al., "Fludized–bed Separators Reviewed: A Low Pressure Drop Approach to Column Chromatography", *Preparative Chromatography*, 1(1), 93–108 (1988).

C.F. Lorenzano–Porras et al., "Relationship between Pore Structure and Diffusion Tortuosity of ZrO$_2$ Colloidal Aggregates", *J. Coll. & Inter. Sci.*, 164, 1–8 (1994).

G. H. Maher et al., "Preparation and Characterization of Ceramic Fine Powders Produced by the Emulsion Process", *American Ceramic Society Bulletin*, 72(5) 72–76 (1993).

J. E. Morris et al. "Preliminary Development of a Thiophilic Zirconia–Based Support for Antibody Purification" (Abstract Only), ACS, Denver, CO (1993).

J. E. Morris et al., "Protein Separations Using HPLC and Fluidized–Bed Zirconia Supports", (Abstract Only), ACS, San Diego, CA (1994).

J. Nawrocki et al., "New Materials for Biotechnology: Chromatographic Stationary Phases Based on Zirconia", *Biotechnol. Prog.*, *10*, 561–573 (1994).

J. Nawrocki et al., "Chemistry of Zirconia and its Use in Chromatography", *J. Chromat. A*, *657*, 229–282 (1993).

M.P. Rigney, "The Development of Porous Zirconia as a Support for Reversed–Phase High–Performance Liquid Chromatography", University of Minnesota Dissertation Abstract, Analytical Chemistry (1989).

M.P. Rigney et al., "Preparation and Evaluation of a Polymer–Coated Zirconia Reversed–Phase Chromatographic Support", *J. Chromatogr.*, *484*, 273–291 (1989).

W.A. Schafer et al., "Physical and Chemical Characterization of a Porous Phosphate–Modified Zirconia Substrate", *J. Chomatogr.*, *587*, 137–147 (1991).

W.A. Schafer et al., "Chromatographic Characterization of a Phosphate–Modified Zirconia Support for Bio–Chromatographic Applications", *J. Chomatogr.*, *587*, 149–160 (1991).

C. Schmidt et al., "Impact of Improved Chromatographic Media on Productivity and Process Design in Downstream Processing", Pharmacia BioProcess Technology AB Company Brochure, Uppsala, Sweden. Available prior to Feb. 27, 1995.

C. Schmidt et al., "Expanded Bed Adsorption — A New Way for Industrial Recovery of Recombinant Proteins", Pharmacia BioProcess Technology AB Company Brochure, Uppsala, Sweden. Available prior to Feb. 27, 1995.

G. Schomburg et al., "Stationary Phases in High Performance Liquid Chromatography", *LC–GC*, *6*, 36–50 (1987).

A. Sköld et al., "Pilot Scale Purification of Recombinant Annexin V using Expanded Bed Adsorption, STREAMLINE™ and Hydrophobic Interaction Chromatography, Butyl Sepharose® 4 Fast Flow", Pharmacia BioProcess Technology AB, Uppsala, Sweden, Available prior to Feb. 1995.

U. Snow, "Adsorbent Reduces Primary Unit Operations for Bioprocess Recovery", *Genetic Engineering News*, p. 16 (1994).

L. Sun et al., "Synthesis of Monodisperse Porous Zirconia Patricles Optimized for HPLC", *Abstracts of Papers*, 14th Minnesota Chromatography Forum, Abstract No. 22, May 4–6 (1992) (Abstract Only).

L. Sun et al., "Polybutadiene–Coated Monodisperse Porous Zirconia Particles for the Separation of Peptides and Proteins", *Abstracts of Papers*, The Pittsburgh Conference, Abstract No. 1243, Mar. 8–12 (1993) (Abstract Only).

L. Sun et al., "Study of Irreversible Adsorption of Proteins on Polybutadiene–coated Zirconia", *Abstracts of Papers*, 15th Minnesota Chromatography Forum, Abstract No.4, May 3–5 (1993) (Abstract Only).

L. Sun et al., "Mobile Phase Effects on the Recovery of Proteins from Polybutadiene–Coated Ceramic Supports", *Abstracts of Papers*, The Pittsburgh Conference, Abstract No. 372, Feb. 27–Mar. 3 (1994) (Abstract Only).

L. Sun et al., "Study of the Irreversible Adsorption of Proteins on Polybutadiene–Coated Zirconia", *J. Chroma A*, *658*, 465–473 (1994).

L. Sun et al., "Synthesis of Porous Zirconia Spheres for HPLC by Polymer–Induced Colloid Aggregation (PICA)," *J. Colloid & Interface Sci.*, *163*, 464–473 (1994).

J. Thömmes et al., "Purificaiton of Monoclonal Antibodies from Whole Hybridoma Fermentation Broth by Fluidized Bed Adsorption", *Biotechnology and Bioengineering*, *45*, 205–211 (1995).

U. Trudinger et al., "Porous Zirconia and Titania as Packing Materials for High–Performance Liquid Chromatography", *J. Chromatogr.*, *535*, 111–125 (1990).

D. A. Ward et al., "Synthesis and Structural Transformation of Zirconia Aerogels", *Chem. Mater.*, *5*, 956–969 (1993).

T. P. Weber et al., "Comparison of Isomer Separation on Carbon–Clad Microporous Zirconia and on Conventional Reversed–Phase High–Performance Liquid Chromatography Supports", *Analytical Chemistry*, *62*(23) 2620–2625.

T. P. Weber et al., "Evaluation of a Zirconia–based Carbon––polymer Composit Reversed–phase Chromatographic Support", *Journal of Chromatography*, *519*, 31–52 (1990).

Wirth et al., "High–performance liquid chromatography of amino acids, peptides and proteins", *Journal of Chromatography*, *646*, 129–141 (1993).

P. Wnukowski et al., Royal Institute of Technology, Stockholm, Sweden and Pharmacia BioProcess Technology AB Company Brochure, Uppsala, Sweden. Available prior to Feb. 1995.

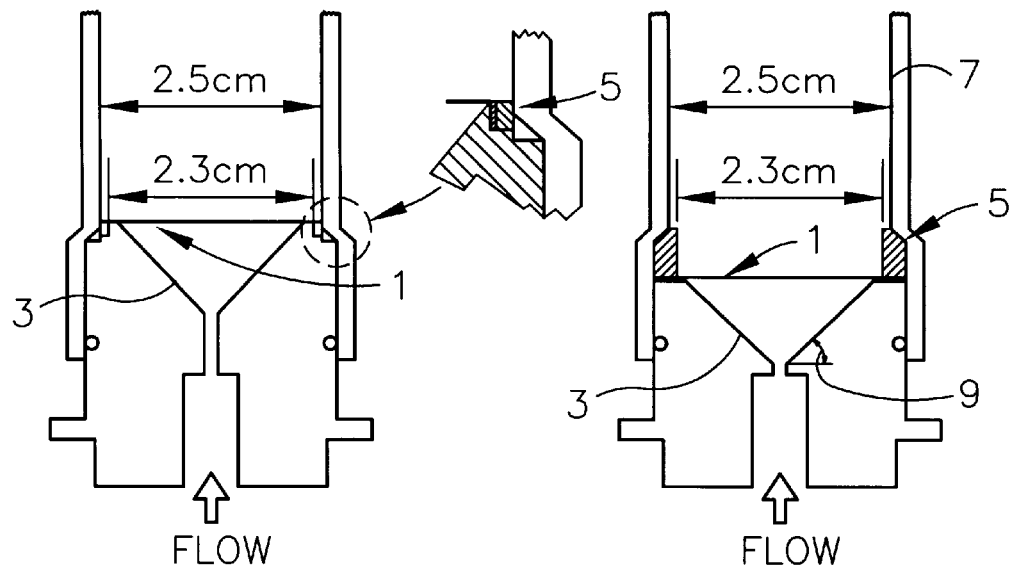
Fig. 1A
Fig. 1B
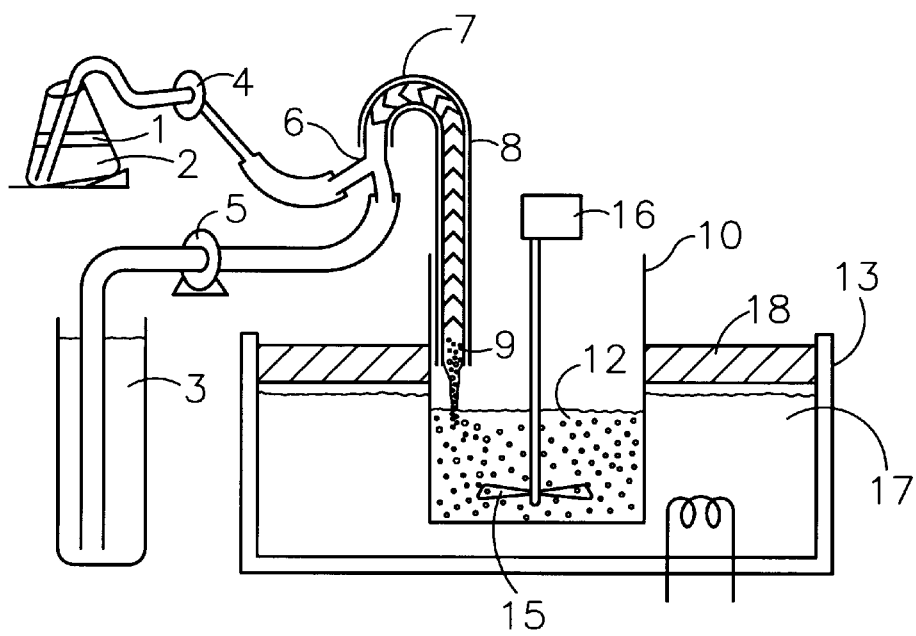
Fig. 2

PROTEIN ADSORPTION BY VERY DENSE POROUS ZIRCONIUM OXIDE PARTICLES IN EXPANDED BEDS

This is a continuation of application Ser. No. 08/394,714, filed Feb. 27, 1995, now U.S. Pat. No. 5,837,826, which is incorporated herein by reference.

STATEMENT REGARDING GOVERNMENT RIGHTS

The present invention was made with government support from the National Science Foundation, under Grant No. CHE-9107029 (June 1991), and from the National Institutes of Health, under Grant No. 5R01-GM45988 (June 1990). The Government has certain rights in this invention.

BACKGROUND OF THE INVENTION

The potential advantages of expanded beds, i.e., fluidized beds, of ion exchange or affinity adsorbents for direct adsorption of proteins from biological process liquids and particulate-containing fluids has been demonstrated. Conventional fluidized bed adsorption systems use 100 μm to 400 μm polymeric or composite particles with small density differences between the adsorbent particles and the liquids being processed. The wide particle size distribution of these adsorbents results in stable beds of particles being classified by the fluid velocity and density. Even though these classified expanded beds are stable, many of these particles are large and have a long characteristic diffusion length (i.e., path length from the outer surface of the particle to the center) within the adsorbent. This results in poor adsorption kinetics. Furthermore, such adsorption particles lack robust ligands with high specificity, are unable to be repeatedly cleaned with harsh reagents, and cannot be used for protein adsorption at elevated temperatures (i.e., greater than about 40° C.). In addition, loss of bed capacity with increasing bed expansion (liquid flow rate) using conventional fluidized bed adsorbents may limit fluidized bed separations due to pore mass transfer resistance.

Solutions to these and other problems associated with conventional fluidized bed systems have included the use of magnetically stabilized fluidized beds (MSFB) and the division of the bed into stages. A more useful approach would be to develop stable adsorbent particles of higher density with appropriate adsorption properties. A need exists for such particles. It is envisioned that with denser particles, higher fluidization velocities (100–250 cm/hour) can be achieved with smaller adsorbent particles. While high flow rates can also be achieved using larger particles (200 μm to 500 μm), fluidization of small particles will minimize bed dispersion and result in more rapid protein adsorption in the presence of entrained particulates such as fermentation broths, cell lysates, blood, or cell culture fluids.

Porous ceramic particles, such as silica, as well as highly crosslinked functionalized organic polymeric materials are used in high performance liquid chromatography for the separation of proteins. However, most of these particles do not have the appropriate density for effective use in expanded or fluidized beds. Furthermore, the ability to repeatedly remove adsorbed protein, nucleic acids, lipids, pyrogenic lipopolysaccharides (LPS), and intact virus or microorganisms (bacteria, fungi or yeast) from such chromatographic media is a challenging problem. This makes these materials undesirable for use in fluidized bed applications because process scale protein adsorbents useful for purification of therapeutic or diagnostic proteins must be capable of repeated clean-in-place cycles. Both the adsorbent and the surface need to be stable to cleaning without loss of capacity or mechanical stability. Such cleaning methods are generally harsh: high or low pH solutions (0.1–2 M NaOH, formic, acetic, peracetic, trifluoroacetic, or hydrochloric acid to 1 M) often in alcohol (70% ethanol or 30% isopropanol); high ionic strength solutions (2 M NaCl or KCl); non-ionic detergents; or high temperature conditions followed by extensive washing with purified, sterilized buffer. Particularly vigorous methods, often at elevated temperatures (e.g., 40–80° C.), are needed to remove and inactivate lipopolysaccharide endotoxin (LPS) and viral nucleic acids from protein adsorbent media because of the extremely low residual levels of these contaminants allowed in human biologics as established by federal regulation and the World Health Organization. Some silica-coated and organic polymeric chromatographic adsorbents tolerate cleaning with 0.1 M sodium hydroxide or ethanol-acetic acid mixtures at refrigerated (4° C.) or ambient temperatures and are more mechanically stable than carbohydrate adsorbents. In general, however, organic polymeric adsorbents cannot be cleaned with harsh agents at elevated temperatures (e.g., 40–60° C.) or sterilized with steam or direct heat. Furthermore, silica chromatographic adsorbents typically cannot be rigorously sanitized, for example, with 0.2 M to 1 M sodium hydroxide, without degradation. In general, silica-based materials are not stable outside the pH range of 2 to 8.

Small (<25 μm) surface-modified porous and highly dense zirconium oxide particles are used in high performance liquid chromatography separations of proteins. See, for example, J. A. Blackwell et al., *J. Chromatogr.*, 549, 59 (1991); J. A. Blackwell et al., *J. Chromatogr.*, 596, 27 (1992); P. W. Carr et al., *Chromatography in Biotechnology*, American Chemical Society, Washington D.C., Symp. Ser. 529, 146 (1993); J. Nawrocki et al., *J. Chromatogr. A*, 657, 229 (1993); and J. Nawrocki et al., *Biotechnol. Prog.*, 10, 561 (1994). Such surface-modified zirconium oxide particles can be modified with a variety of Lewis bases. Only certain of these surface-modified zirconium oxide particles, however, are capable of withstanding the repeated harsh cleaning conditions required for process scale separation of polypeptides and proteins destined for therapeutic use. Furthermore, such particles do not have the appropriate particle size for effective use in an expanded fluidized bed.

Although larger zirconium oxide particles (1 μm to 1 cm), have been suggested as suitable for use in fluidized beds (see, U.S. Pat. Nos. 5,108,597, 5,271,833, and 5,346,619), these particles are either carbon-clad or carbon-clad with a crosslinked polymer. Such surface-modified zirconium oxide particles are used for reversed phase separations and are not generally suitable for expanded bed and most process scale protein separations. See, for example, C. H. Lochmüller et al., *Preparative Chromatography* 1, 93 (1988). Furthermore, protein adsorption at elevated temperatures and repeated cleaning of these particles with strong base (0.2 M to 1.5 M NaOH) has not been disclosed. Thus, a need exists for adsorbent particles of the appropriate particle size, density, porosity, and high temperature stability for use in process scale expanded beds for purification of therapeutic or diagnostic proteins.

SUMMARY OF THE INVENTION

The present invention provides a system and method of separating a target protein from a feedstock in an expanded bed. This method includes the steps of: expanding a bed of surface-modified zirconium oxide particles, wherein the surface-modified zirconium oxide particles have a capacity factor greater than about 10 (preferably greater than about 20 and more preferably greater than about 50) and comprise a core zirconium oxide particle having a particle size of about 30–400 µm (preferably 50–200 µm) and a specific gravity of about 2.5–3.5 g/cm$^3$ (preferably about 3.0–3.5 g/cm$^3$); eluting the feedstock through the expanded bed to adsorb the target protein to the surface-modified zirconium oxide particles; and removing the target protein from the surface-modified zirconium oxide particles. Preferably, the surface-modified zirconium oxide particles comprise an ion-exchange phase, such as a Lewis base, examples of which include fluoride, phosphate, citrate, maleate, EDTA, EGTA, CDTA, borate, polyphosphate, dicarboxylic acid, and tricarboxylic acid; or an affinity phase such as hydrophilic polymer, such as a polyamino acid, or a carbohydrate polymer having covalently bound affinity ligands, examples of which include a carbohydrate polymer, such as dextran, having covalently bound triazine dyes, thiophilic ligands, or other nonprotein affinity ligands.

Advantageously, the step of eluting the feedstock through the expanded bed to adsorb the target protein to the surface-modified zirconium oxide particles is preferably carried out at a linear fluid velocity of at least about 100 cm/hour, and the step of removing the target protein from the surface-modified zirconium oxide particles is preferably carried out without reversing the flow of the eluent. Significantly, the binding capacity of the expanded bed of surface-modified zirconium oxide particles at 1% breakthrough is preferably at least about 20 mg protein/ml settled bed volume and the terminal settling velocity is preferably about 2–4 mm/second in water at ambient temperatures.

The method of the present invention is advantageous because the feedstock containing the target protein can include entrained solids, e.g., cells or cellular debris, such as bacteria, yeast or blood cells. If desired, the step of eluting the feedstock through the expanded bed is carried out at a temperature greater than about 30° C., preferably greater than about 50° C., which is particularly advantageous for very viscous feedstocks that flow at elevated temperatures.

Advantageously, the method can further include a step of cleaning the surface-modified zirconium oxide particles with a strong base, e.g., 0.2 M NaOH, which can be repeated with little or no deterioration of the particles. For certain surface modifications, a strong base will strip the particles of the surface modification. If this occurs, the surface modified particles can be regenerated by contacting the cleaned particles with a surface-modifying material, e.g., NaF.

The present invention also provides a method for producing inorganic particles using a series of steps referred to herein as the surfactant oil emulsion (SOM) method. This method includes the steps of: dispersing an aqueous sol comprising a colloidal dispersion of inorganic particles with a forming/extracting medium comprising a nonionic surfactant; heating the dispersion of the aqueous sol and forming/extracting medium to extract water from the sol and form aggregates of sol particles; collecting the aggregates; washing the aggregates; and sintering the aggregates at a temperature and for a time effective to increase their mechanical strength. Preferably, the forming/extracting medium comprises peanut oil, and more preferably a mixture of peanut oil and oleyl alcohol. Preferably, the step of heating comprises heating at a temperature of about 80–100° C.

The present invention also provides a method for producing inorganic particles using a series of steps referred to herein as the fed batch oil emulsion (FBOM) method. This method includes the steps of: dispersing an aqueous sol comprising a colloidal dispersion of inorganic particles in a forming medium using an in-line mixer to form an emulsion; combining the emulsion with an extracting medium to extract water from the sol and form aggregates of sol particles; collecting the aggregates; washing the aggregates; and sintering the aggregates at a temperature and for a time effective to increase their mechanical strength. In this FBOM method, as opposed to the SOM method, the forming and extracting media are used to separate the emulsion step from the drying step. In the FBOM method, although they can be, the forming and extracting media are not the same media Also, provided are the sintered porous $ZrO_2$ particles prepared by the FBOM and SOM methods.

The following abbreviations are used throughout: $AFS_{280}$=full scale absorbance at $280_{nm}$; BSA=bovine serum albumin; C=bulk protein concentration; $C_o$=column inlet protein concentration; $C_t$=UV monitor voltage; CDTA= cyclohexanediaminetetraacetic acid; $(D_{ax})_{app}$=apparent axial dispersion coefficient; DBC=dynamic binding capacity, $C/C_o$; $\epsilon$=bed voidage; EDTA= ethylenediaminetetraacetic acid; EGTA=ethylene glycol-bis (β-aminoethyl ether)N,N,N',N'-tetraacetic acid; FBOM=fed batch oil emulsion; H=bed height; LPS=lipopolysaccharide; $m_o$=tracer peak zeroth moment; MES=2-morpholinoethanesulfonic acid monohydrate; MSFB= magnetically stabilized fluidized bed; OEM=oil emulsion synthesis; Q=volumetric flow rate in tracer studies; RTD= residence time distribution; SOM=surfactant oil emulsion synthesis; Δt=tracer peak data acquisition time interval; u=superficial liquid velocity; and $u_t$=particle terminal settling velocity. As used herein, an expanded bed and a fluidized bed are used interchangably, without limitation as to particle size distribution of the adsorbent in the bed.

BRIEF DESCRIPTION OF THE DRAWINGS

FIGS. 1A–1B. 45° cone flow distribution for ascending fluidization of porous zirconia particles.

A. Stainless steel screen held in place with sealing ring.

B. Flat screen held in place with teflon ring.

FIG. 2. Schematic of the Fed Batch Oil Emulsion (FBOM) process.

Figure 3A:
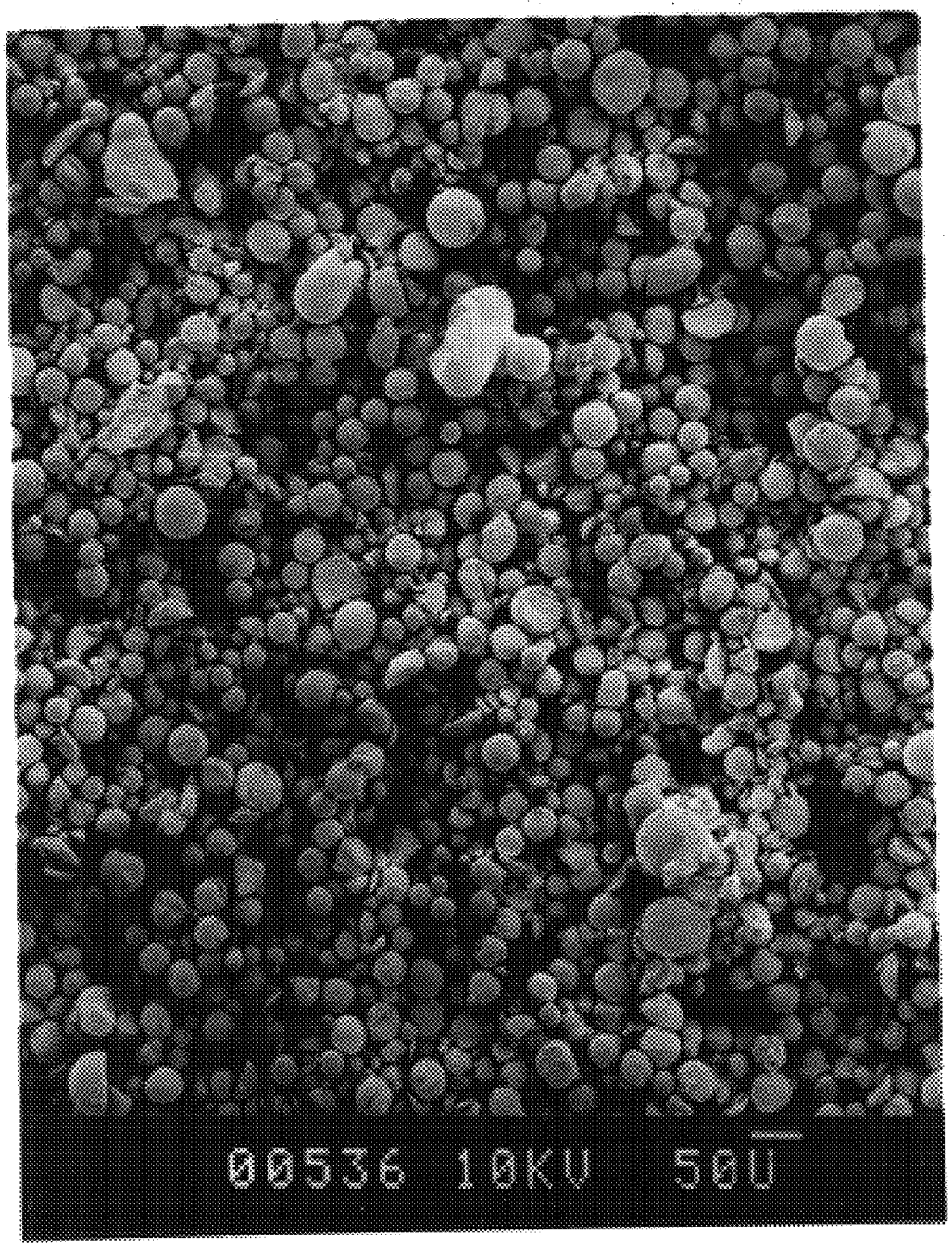
Figure 3B:
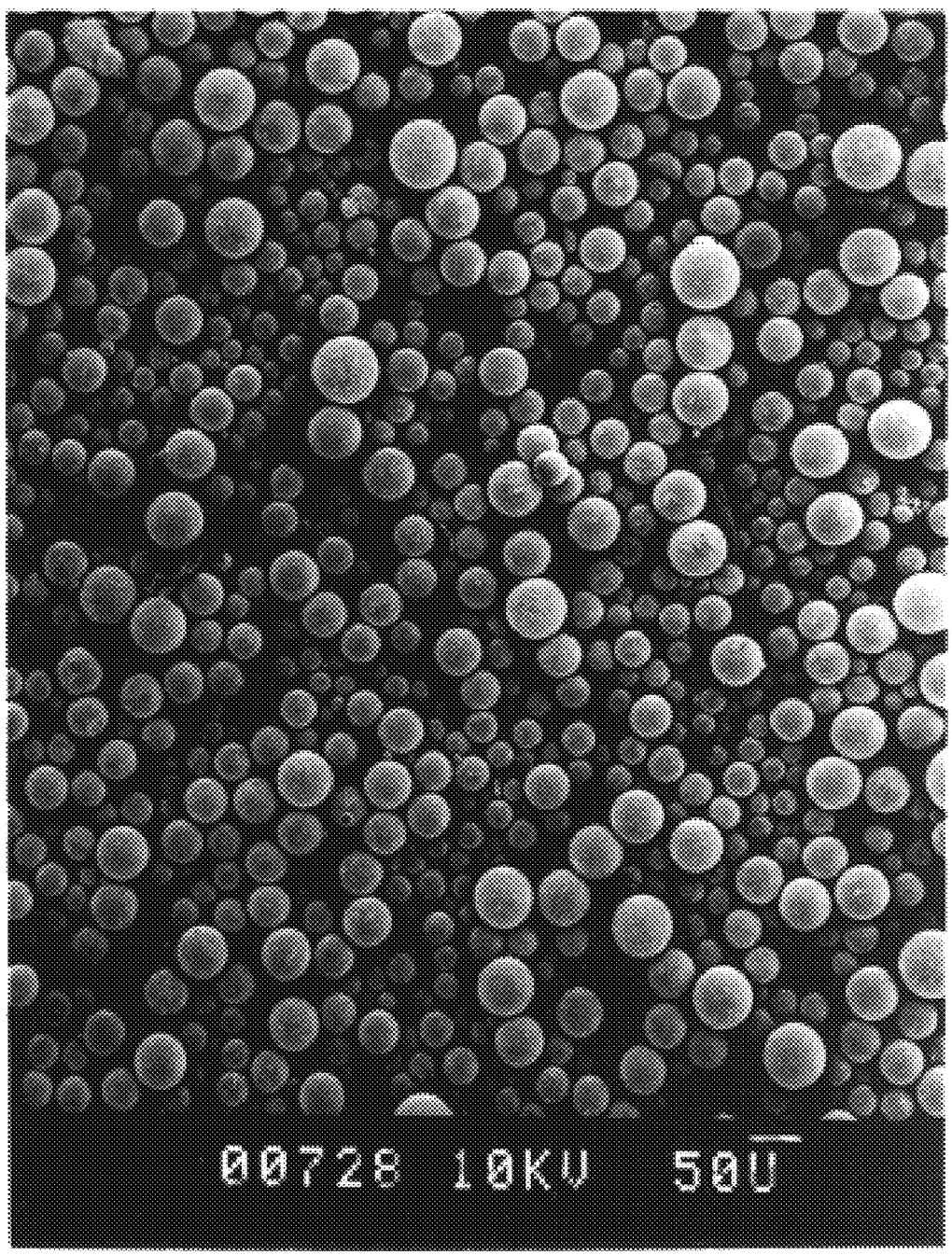

FIGS. 3A–3B. SEM of (A) SOM particles and (B) FBOM particles (magnification 100×).

Figure 4:
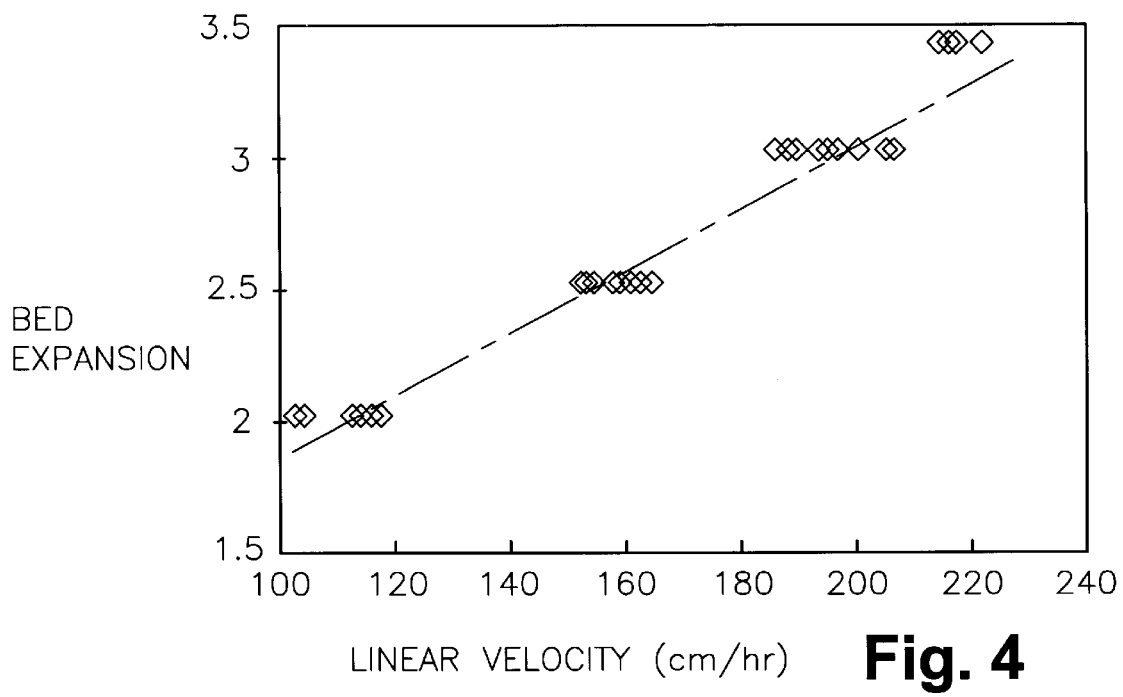

FIG. 4. Bed expansion as a function of linear velocity. Combined SOM particles, 4 mg/ml BSA in MES loading buffer.

Figure 5A:
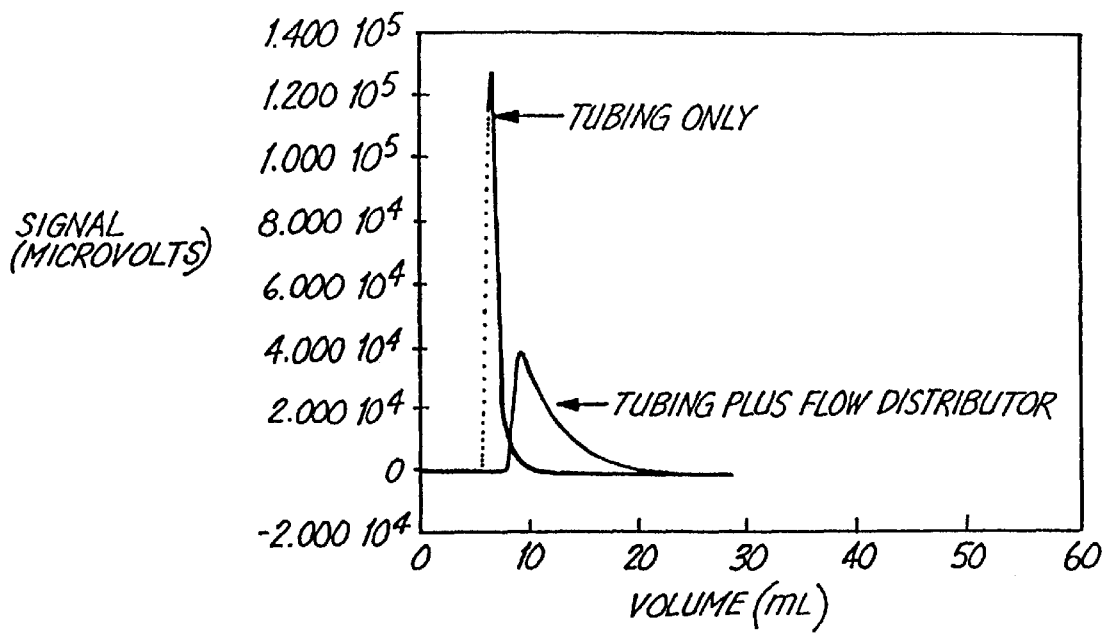
Figure 5B:
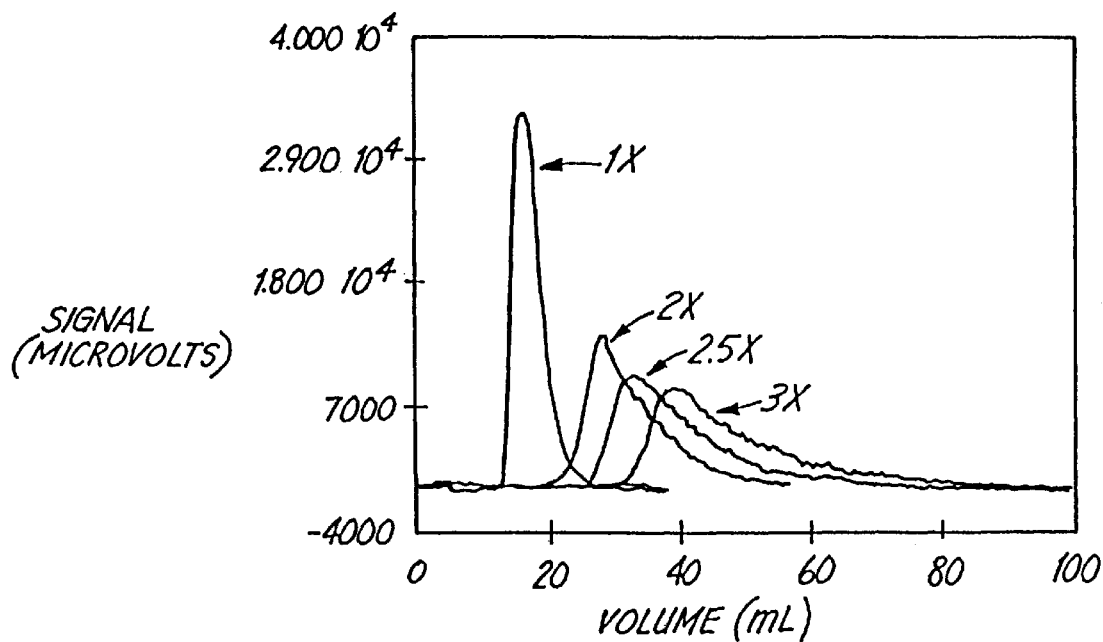
Figure 6A:
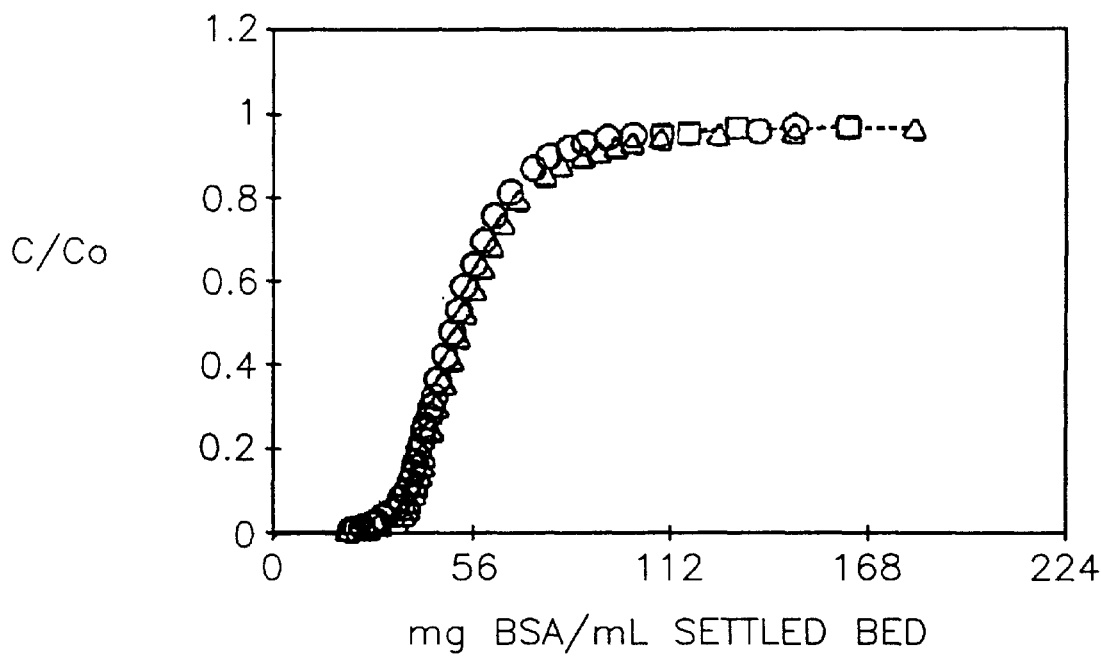
Figure 6B:
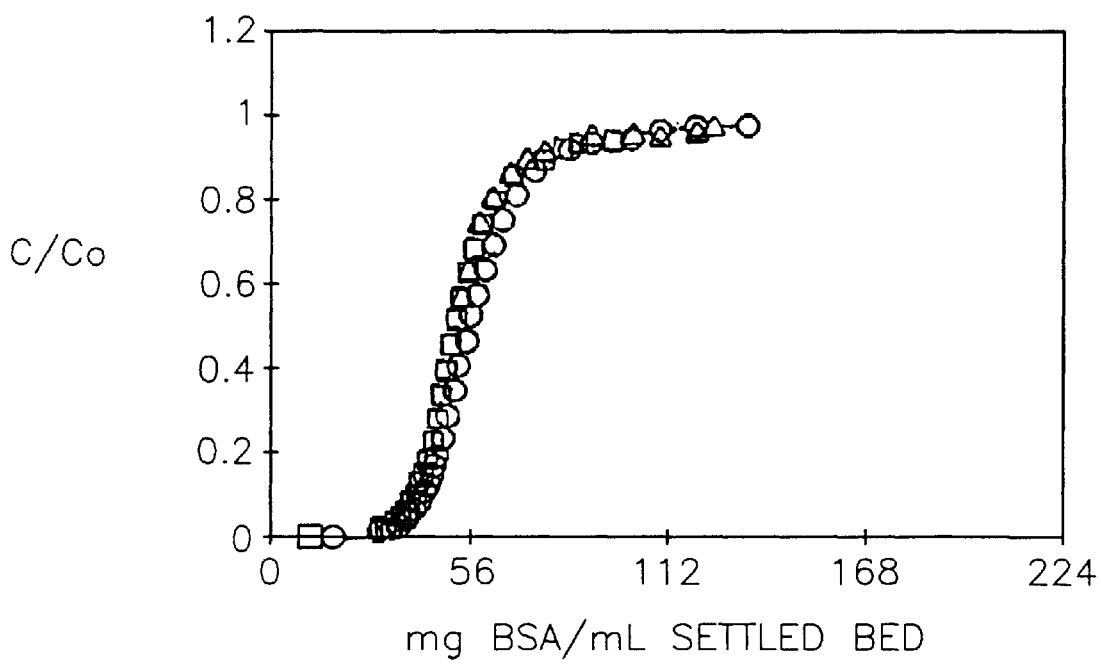
Figure 6C:
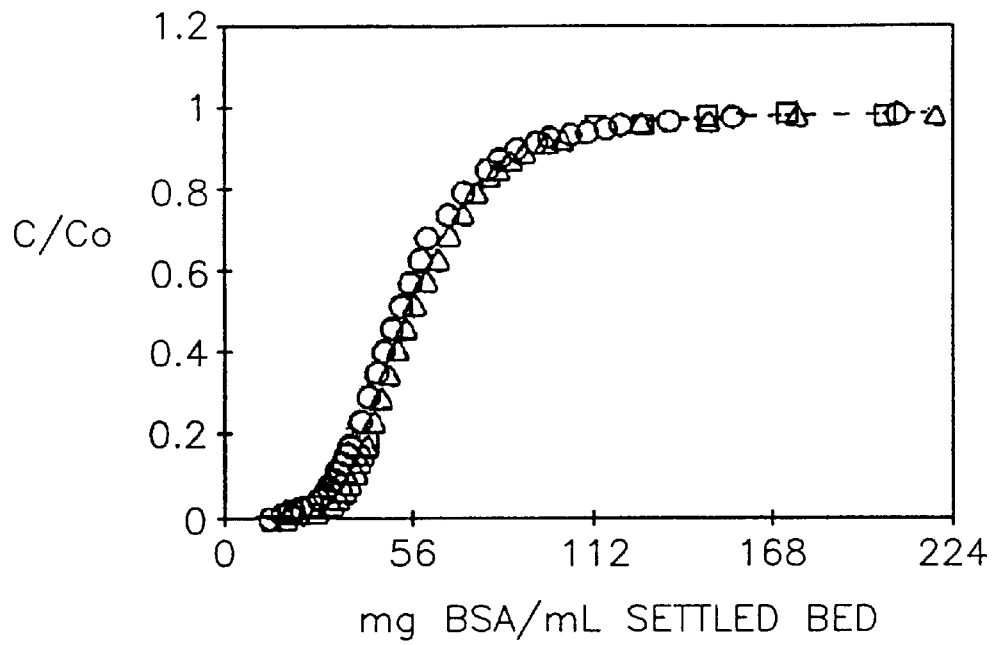
Figure 6D:
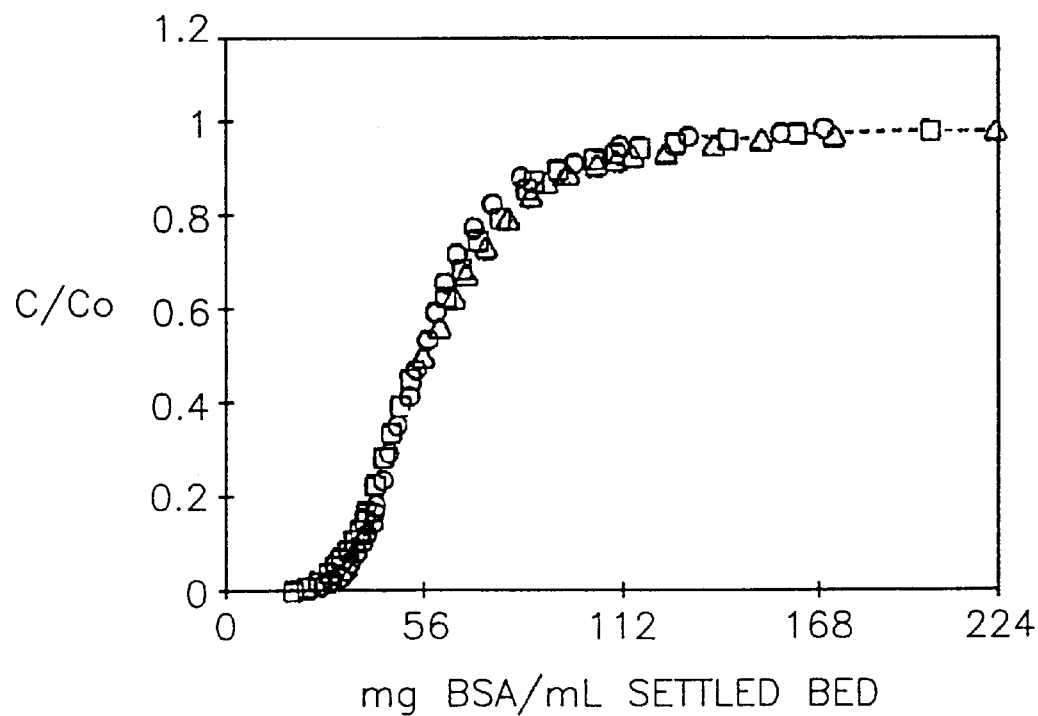

FIGS. 5A–5B. Tracer residence time distributions as a function of flow distributor geometry with and without particles in the column.

A. Flow system without particles, 45° inlet flow adaptor; flow rate 9.5 ml/minute; nitrate tracer.

B. Flow system with particles, 45° inlet flow adaptor; 1× and 2×, flow rate 9.5 ml/minute; 2.5× flow rate 13.5 ml/minute; 3× flow rate 18.8 ml/minute; nitrate tracer.

FIGS. 6A–6D. Adsorption breakthrough for BSA by fluoride adsorbed combined SOM particles as a function of bed expansion. Symbols represent triplicate determinations. Settled bed height 2.3 cm.

A. Packed bed; $C_o$=4.2 mg/ml; fluid velocity=109 cm/hour.

B. 2× expansion; $C_o$=3.9–4.0 mg/ml; fluid velocity=110 cm/hour.

C. 2.5× expansion. $C_o$=4.0–4.1 mg/ml. Fluid velocity= 158 cm/hour.

D. 3× expansion. $C_o$=4 mg/ml. Fluid velocity=200 cm/hour.

Figure 7A:
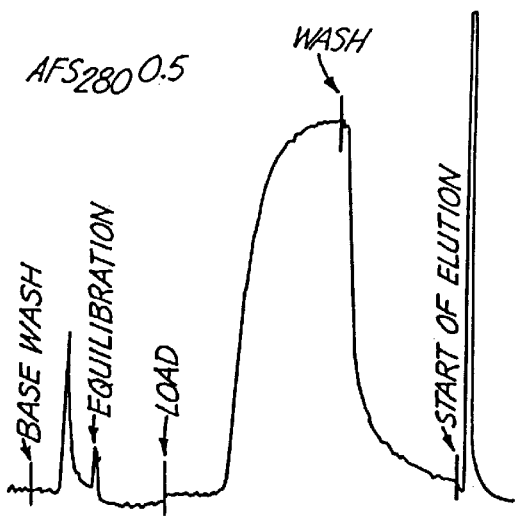
Figure 7B:
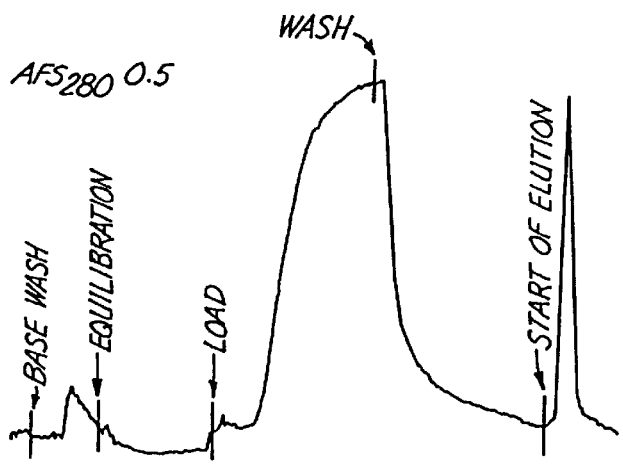
Figure 7C:
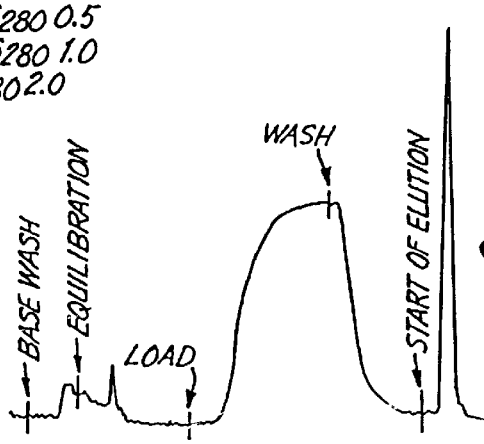

FIGS. 7A–7C. BSA adsorption/elution cycle using fluoride adsorbed SOM A particles (50 μm) and a 2.5 cm bed diameter. Settled bed height 2.1 cm. The full scale absorbance ($AFS_{280}$) for washing, equilibration, and loading=0.5. $AFS_{280}$ for elution=2.0, except for (C) where $AFS_{280}$ for washing and loading=1.0.

A. Packed bed; $C_o$=4.0 mg/ml; fluid velocity=109 cm/hour; load=50 mM MES, 100 mM NaF; elution=50 mM MES, 100 mM NaF, 750 mM $Na_2SO_4$; wash=0.1 M NaOH.

B. 2× bed expansion; $C_o$=4.0 mg/ml; fluid velocity=107 cm/hour; load=50 mM MES, 100 mM NaF; elution=50 mM MES, 100 mM NaF, 750 mM $Na_2SO_4$; wash=0.1 M NaOH.

C. 3× bed expansion; $C_o$=4.0 mg/ml; fluid velocity=215 cm/hour; load=50 mM MES, 100 mM NaF; elution=50 mM MES, 100 mM NaF, 750 mM $Na_2SO_4$; wash=0.1 M NaOH.

Figure 8:
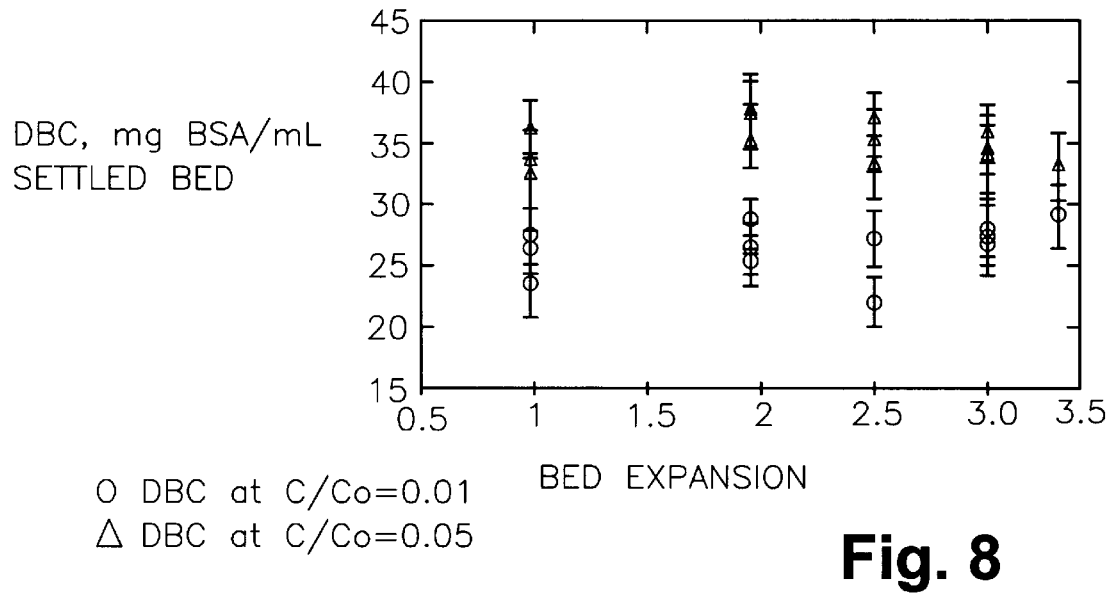

FIG. 8. Dynamic BSA binding capacity of fluoride adsorbed SOM A & B particles as a function of bed expansion. Breakthrough calculated following the method of Chase and Draeger, *J. Chromatogr.*, 597, 129 (1992); •, $C/C_o$=1%; ▲, $C/C_o$=5%.

Figure 9:
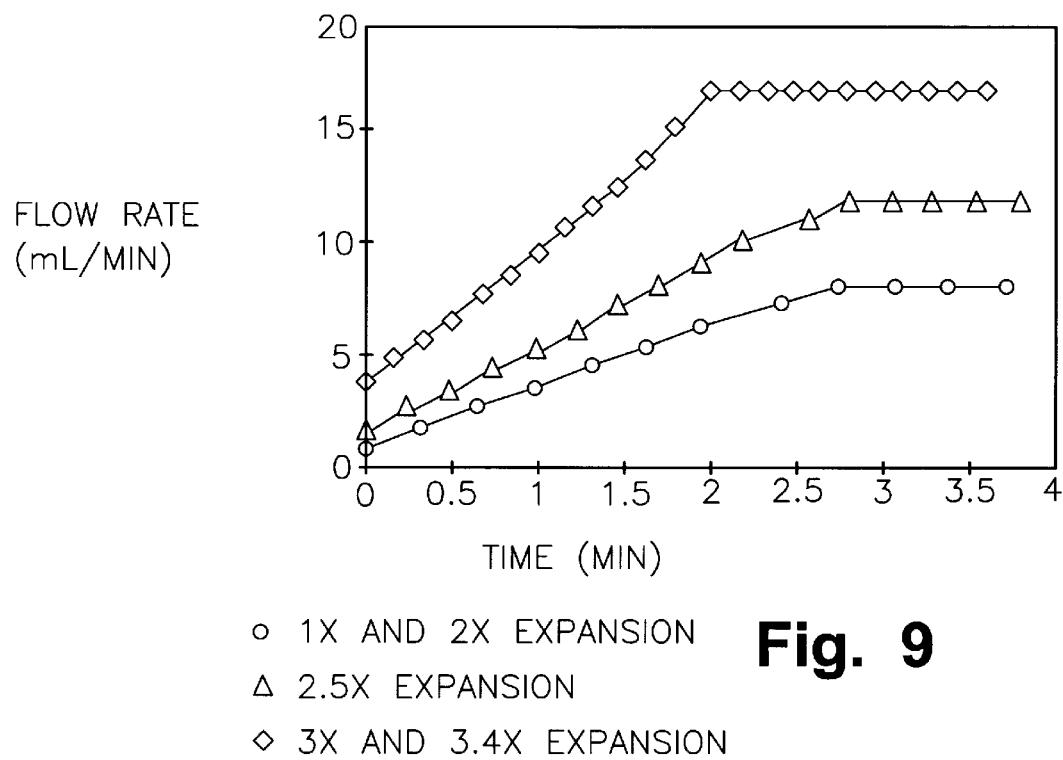

FIG. 9. Time required to increase flow rate to final fluidization velocity during BSA adsorption on fluoride adsorbed SOM A & B particles. $C/C_o$≈4 mg/ml; •, settled bed and 2× expansion; ▲, 2.5× bed expansion; ♦, 3× and 3.4× bed expansion.

Figure 10A:
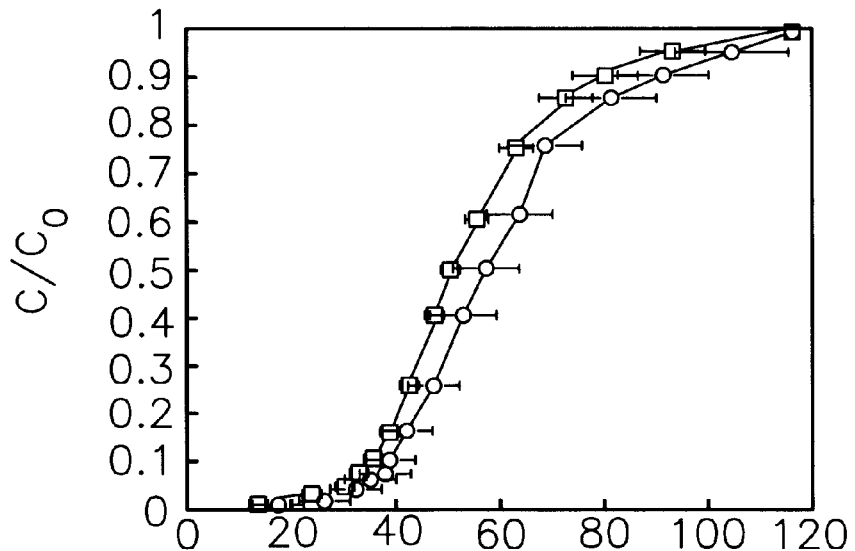
Figure 10B:
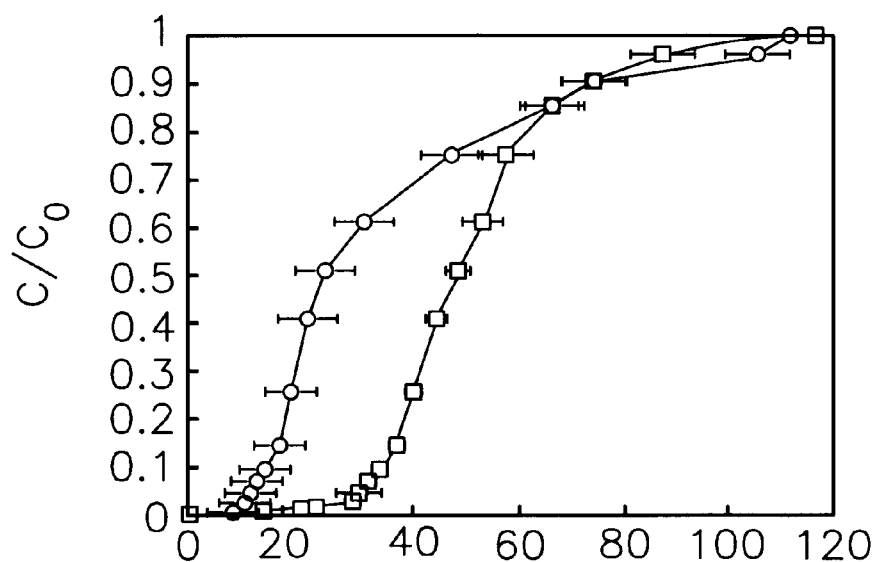

FIGS. 10A–10B. The effect of flow disruption geometry and particle clumping on BSA binding capacity by fluoride adsorbed SOM A particles.

A. Comparison of stainless steel frit and 8 μm screen; bed expansion 2×; ■, stainless steel frit. DBC at $C/C_o$=0.05, 30±2 mg/ml settled bed volume; •, screen (configuration A, FIG. 2). DBC ($C/C_o$=0.05) 31±2 mg/ml settled bed volume.

B. The effect of particle clumping on DBC. Bed expansion 2×. •, clean particles, no clumping (screen configuration B, FIG. 2). DBC ($C/C_o$=0.05) 32±4 mg/ml settled bed vol. ■, clumped particles. DBC ($C/C_o$=0.05) 9±2 mg/ml settled bed vol.

Figure 11:
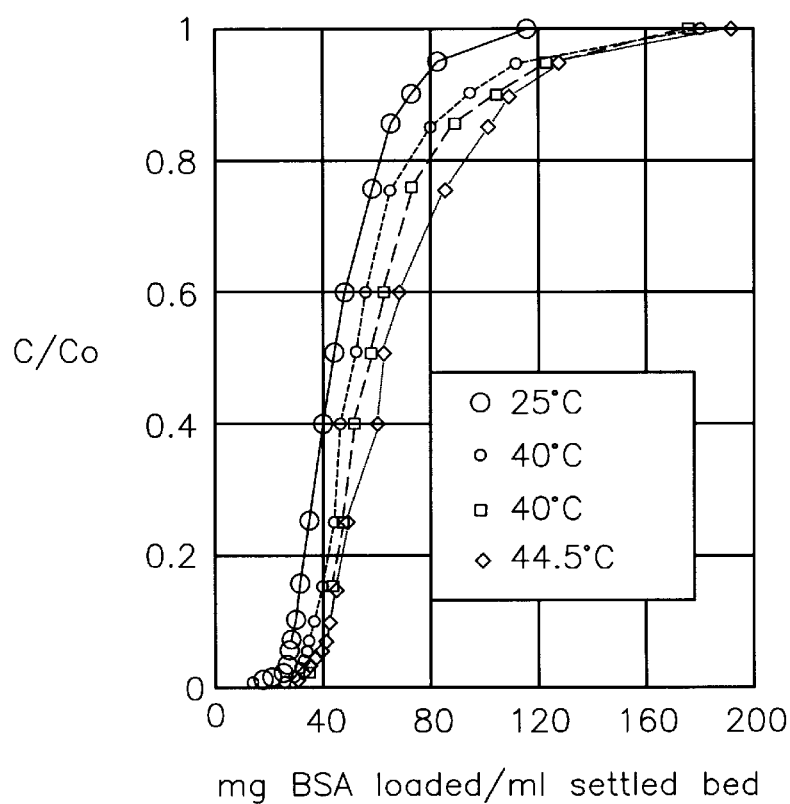

FIG. 11. Adsorption breakthrough for BSA by fluoride adsorbed SOM particles at elevated temperatures (2× bed expansion).

DETAILED DESCRIPTION OF THE INVENTION

The present invention provides an expanded bed process and system that includes an adsorbent material that is exceedingly mechanically stable at temperatures in excess of 40° C.; base-stable (i.e., such that it can withstand repeated cleaning with base as described below); sufficiently dense and of an appropriate particle size for effective fluidization resulting in stable bed expansion; and sufficiently porous for separation of proteins from large volumes of fluids. This adsorbent material possesses a significantly high and surprisingly substantially consistent dynamic protein binding capacity when expanded at high fluid velocity (i.e., greater than about 100 cm/hour). Thus, it can be used to adsorb proteins much more rapidly in expanded beds than either inorganic-composite or crosslinked carbohydrate polymeric particles. Furthermore, the expanded bed adsorbent material of the present invention can significantly reduce column cycle time (equilibration, loading to breakthrough, washing, protein elution, cleaning), and cost, in processing large volumes of protein-containing process fluids. It can also be used advantageously for adsorbing proteins from a viscous material that must be heated to flow, such as a concentrated sugar syrup, and for adsorbing proteins from a solids-containing process stream such as cell homogenates, culture fluid, or milk.

In an expanded (or fluidized) bed, a sedimented bed of an adsorbent is expanded by upward flow of a liquid fluidization medium, e.g., water, buffer, or other aqueous media, in a column (typically, a vertically held column with a solution inlet in its bottom portion and a solution outlet in its top portion) with a flow distribution system designed to reduce axial mixing. When the bed is stably expanded, as defined below, and has expanded at least greater than 1× times (typically up to 3× times) its original sedimented bed height, a feedstock is applied. As the feedstock passes through the expanded bed, the target protein, which is either to be removed as a contaminant or collected as a desired product, is adsorbed onto the adsorbent material and the remaining feedstock material, which can be in the form of solids such as cells or cellular debris, passes through. In standard expanded beds, the flow is then reversed to elute the target protein from the sedimented adsorbent. Although this can be done in the system and process of the present invention, the eluent flow does not need to be reversed. That is, advantageously the target protein can be eluted quickly and effectively without changing the direction of flow, or the flow rate.

The parameters influencing the efficiency of the separation in an expanded bed include the type of adsorbent material (e.g., size, density, and surface properties), the feedstock properties (e.g., viscosity, biomass content, temperature, etc.), and the flow distributor design. The expanded bed adsorbent material described herein produces a stable bed, i.e., a bed of stably suspended particles. That is, there is generally no apparent internal circulation, i.e., no visible boiling on the surface or internal jets. Furthermore, there are no detectable particles or fines in the effluent and no detectable clumping of the particles which would cause mixing and nonuniform liquid flow through the bed reducing protein binding capacity. This bed stability can be maintained in extremely shallow beds (i.e., less than 1:1 height to diameter) with high flow rates, i.e., at least about 100 cm/hour, with low pressure drops and without magnetic bed stabilization.

Furthermore, the expanded bed adsorbent material described herein has a significantly high and surprisingly substantially constant dynamic protein binding capacity even at high fluid velocities. That is, at 1% breakthrough, i.e., the point at which 1% protein appears in the effluent, the binding capacity under flow conditions is at least about 20 mg protein/ml settled bed volume, preferably at least about 25 mg protein/ml settled bed volume. The "settled bed volume" is the volume of a bed of particles settled by gravity in an aqueous media For use in rapid process scale separation, binding capacities need to be well in excess of 5–10 mg protein/ml settled bed volume. Also, the dynamic protein binding capacity of the expanded bed adsorbent material described herein increases with increasing temperature.

The expanded bed system described herein is significantly fast at processing proteins. That is, large amounts of protein can be loaded on a shallow bed (i.e., a bed of 1:1 height to diameter or less) in a short period of time. For example, 250–400 mg of protein can be completely adsorbed on 10 ml of adsorbent material of the present invention in under 10 minutes.

The expanded bed adsorbent material of the present invention includes particles having a zirconium oxide core, the surface of which is modified for protein separation applications with a surface-modifying material. The preferred core zirconium oxide particles are generally spherical and can be referred to as "spherules." Thus, the terms "particle" and "spherule" are used herein interchangeably. Although particles made by the preferred process described below have very few flattened portions or indentations, such deviations from perfect spherical particles are tolerated in expanded bed applications. Thus, the present invention is also intended to encompass irregularly shaped particles. The core zirconium oxide particles are chemically and mechanically stable in an aqueous system having a wide pH range (i.e., pH 1–14) and/or under extreme temperatures (e.g., autoclaving temperatures and even temperatures as high as 500° C.). They are typically strong enough to withstand an expanded bed system with substantially no decomposition or generation of fines. Such stability allows protein separation from viscous liquids that require heat to readily flow through a fluidized bed.

The mean particle size of the core zirconium oxide particles is within a range of about 30–400 μm. Below this particle size, the particles become entrained in the eluent, and above this particle size, the particles will not fluidize. Preferably, the mean particle size of the core zirconium oxide particles is about 40–300 μm, and more preferably about 50–200 μm. As used herein, "particle size" is defined by the average of the longest dimension of each particle and can be measured by any conventional technique. Preferably, this is the average "diameter" of the particles because preferred particles are generally spherical in shape. Thus, the terms "diameter size," and "particle size" are used interchangeably.

The core zirconium oxide particles have a specific gravity (i.e., the effective particle density during fluidization or water-filled density) of about 2.5–3.5 $g/cm^3$, preferably about 3.0–3.5 $g/cm^3$. Neither the particle size nor the specific gravity are changed significantly when the surface of the particles is modified for protein separations. Particles of this range of particle size and density can be fluidized at high flow rates (i.e., at least about 100 cm/hour) and form a stable bed without magnetic bed stabilization.

The core zirconium oxide particles have generally uniform pores, the diameter of which depends on the size of the colloidal particles used in their preparation and on the process for bringing the colloid together to form large pore spherules. The larger the colloidal particles, the larger the pores between them in the spherules. Typically, the pores are less than about 0.15 μm (1500 Å) in diameter. Preferably, for protein separation applications, the particles have a pore size of about 200–1000 Å, more preferably about 400–1000 Å, and most preferably about 800–1000 Å. For preferred embodiment, the pore size distribution is also generally relatively narrow. Preferably, greater than about 70% (and more preferably greater than about 90%) of the pores have a pore size within a range that spans ±50% of the average pore size. The void fraction is preferably greater than about 0.4, and more preferably greater than about 0.5.

Because bare zirconium oxide particles bind proteins irreversibly, the zirconium oxide particles used in expanded bed applications are modified to reversibly bind proteins. Modified particles having a high specific affinity are suitable for expanded bed applications. Modified particles with a high specific affinity have a large capacity factor, k', which is the measure of the strength of adsorption. That is, k' is the fraction of the solute in the adsorbed phase over the fraction of solute in the solution phase. For an expanded bed adsorbent material, the capacity factor k' should be high in the loading phase and low (preferably less than 1, and ideally 0) in the washing phase. This can be adjusted by controlling the elution conditions, and is well known to one of skill in the art.

Such modified particles, i.e., those with a high specific affinity, include those capable of adsorbing proteins using an ion-exchange mechanism or an affinity mechanism. Such particles are referred to as having an ion-exchange phase and an affinity phase, respectively. Such materials have a capacity factor of greater than about 10, preferably greater than about 20, and more preferably greater than about 50. Excluded from such materials are reversed-phase materials, e.g., carbon-coated particles, and materials coated with hydrophobic polymers. Examples of suitable coating materials include carbohydrate polymers, such as dextran or cellulose, with covalently bound triazine dyes, thiophilic ligands, and other nonprotein affinity ligands, hydrophilic polymers such as polyethyleneimine and polyamino acids, and hard Lewis bases such as fluoride, phosphate, maleate, citrate, EDTA, EGTA, CDTA, borate, polyphosphates, di- or tri-carboxylic acids. It should be noted that ion-exchange coating materials are less desirable than affinity coating materials for use in the direct recovery of many proteins from fermentation broths or cell culture fluids, due to the high ionic strength of these fluids and the resulting low adsorbent capacities.

These modified particles must be base-stable. As used herein, base-stable means that the particles must withstand repeated cleaning with base (e.g., 0.2 M to 1.5 M NaOH) at ambient or elevated temperatures (e.g., up to about 100° C.) without significant deterioration. This does not mean, however, that the material modifying the surface is not removed by base. It can be, as long as the surface modification is easily regenerated. For example, the significant base stability of fluoride-modified particles allows sterilization of the material and stripping of bound proteins with 0.2 M sodium hydroxide solutions. Although such treatments strip all adsorbed materials, including fluoride, equilibration of the stripped particles with a fluoride solution of the desired ionic strength and pH restores the selectivity and efficiency of the expanded bed adsorbent material to its original condition. In preferred embodiments, this cycle of sorption and stripping can be repeated indefinitely with substantially no loss of efficiency or selectivity. Thus, although ion-exchange phases may be less desirable than affinity phases when used in expanded beds, the fluoride-modified zirconium oxide particles are a convenient, easily cleaned and regenerated adsorbent material.

The surface-modified porous zirconium oxide particles with the prescribed particle size and density described above are well suited for fluidization, even in beds with height to diameter ratios of slightly less than 1.0. With conventional fluidized bed materials, e.g., organic polymers or silica, a bed with a height to diameter ratio of at least 3:1 is required. Using the surface-modified zirconium oxide spherules described herein, stable expanded beds of classified particles over a range of linear fluid velocities at least about 100 cm/hour, and as high as 4000 cm/hour, can be attained. Typically, for 50 μm particles, a linear fluid velocity of about 100–400 cm/hour for a 2× expansion is possible, preferably it is about 100–200 cm/hour. For 150 μm particles, a linear fluid velocity of 700 cm/hour for a 2× expansion, and 1750 for a 3× expansion, are possible. For 200 μm particles, a linear fluid velocity of 1350 cm/hour for a 2× expansion, and 3100 for a 3× expansion, are possible. Thus, using the adsorbent material described herein, the speed at which proteins can be adsorbed and feedstocks can be processed provides a significant advantage.

The terminal settling velocity, $u_t$ (i.e., the maximum velocity at which the particles will settle under the influence of gravity), of useful particles is about 2–4 mm/second, preferably about 2.7–3.3 mm/second, in water at ambient temperatures (i.e., 25–30° C.). This is considerably faster that the terminal settling velocity of commercially available 100–300 μm DEAE particles (available under the tradename STREAMLINE™ from Pharmacia, Inc., Uppsala, Sweden) of 0.7 mm/second. The minimum velocity at which the particles are fluidized will be slightly higher than the terminal settling velocity. A particle with a low terminal settling velocity will be fluidized at a low velocity and hence the throughput to the system will be low (the rate at which protein can be adsorbed).

Although the adsorbent material described above is particularly advantageous for fluidized bed applications, the stability of the expanded beds and the ability to clean the particles can be affected by the flow distribution geometry. Thus, a unique inlet flow distribution system was created to enhance the effectiveness of the modified zirconium oxide particles by reducing the back-mixing caused by radial velocity differences during fluidization in the column. This system includes an inlet flow distribution system as shown in FIG. 1B. FIG. 1A is shown for comparison purposes as this arrangement resulted in turbulent mixing. In FIG. 1B, an inlet screen 1, such as a ceramic, stainless steel, or other base-resistant screen, is attached to a conical- or dish-shaped end fitting 3 with a sealing ring 5 inside a column 7, such as a glass or stainless steel column. The inlet screen 1 is attached inside the column 7 with the sealing ring 5 in a manner that reduces turbulence, e.g., back-eddies, above the sealing ring 5. The design shown in the exploded view of FIG. 1A, wherein the screen is bent and the top of the sealing ring is at the level of the screen, or slightly below, causes such turbulence. Thus, the design shown in FIG. 1B is preferred. The top of the conical- or dish-shaped end fitting 3 is preferably of the same diameter as the internal diameter of the column 7, although it can be slightly less, and the angle 9 is at least about 45°, although it can be greater.

The present invention also provides methods for the preparation of porous zirconium oxide particles. For purposes of the present invention, an adequate method is one that yields generally mechanically and chemically stable porous particles. Various colloid-aggregation processes can be used for the preparation of the porous zirconium oxide spheres described above. Preferred methods are based on an oil emulsion technique, which involves mechanically dispersing micron-scale droplets of an aqueous zirconia sol of colloidal particles in an oil phase. Gelation of the colloids within the droplet and extraction of water from the droplets yields zirconia aggregates that are further strengthened by sintering. The larger the colloidal granules used in the formation of the aqueous sol, the larger the resulting pore diameters. These methods produce a polydisperse collection of spheres. Such particles are preferably produced in a yield of greater than about 30%, more preferably greater than about 50%, and most preferably greater than about 70%. Yields greater than about 90% are possible with the fed batch oil emulsion process described below.

In one oil emulsion method, referred to herein as the surfactant oil emulsion ("SOM") method, the extraction and gelation occur as the emulsion is being continuously formed. A nonionic surfactant is used to help control the final particle size. Specifically, the method involves dispersing an aqueous sol containing a dispersion of colloidal zirconia ($ZrO_2$) particles into droplets distributed in a forming and extracting medium that will extract water from the dispersed sol and form droplets. This forming/extracting medium includes a substantially nonpolar liquid or mixture of liquids that will form an emulsion with the polar sol and that also has sufficient polar character to extract water from the sol droplets. The colloidal sol contains a nonionic surfactant to stabilize the droplet sizes that will result in particles of the desired size. Optionally, the forming/extracting medium can include a base or the sol can include a water-soluble base precursor, e.g., urea, to induce gelation of the sol droplets before they dry. All or a portion of the water is removed with heating while stirring at high speeds to reform droplets as they coalesce. The drying results in gelled, solid spherules that consist of aggregated colloid particles that can be conveniently separated from the medium by any suitable method, e.g., filtration.

The forming/extracting medium for the SOM method includes a substantially water-insoluble, high molecular weight oil, a long-chain, substantially oil-miscible alcohol or ketone, or mixture thereof. The oil, alcohol, and ketone can have substantially carbon-based backbones or silicon-based backbones. Preferably, the SOM forming/extracting medium includes a mixture of an oil and an alcohol or a ketone. The oil can be any oil with a sufficiently high molecular weight such that it has a very low volatility but is reasonably fluid. Examples of suitable oils include vegetable oils, such as peanut oil, corn oil, olive oil, as well as silicone oils, and hydrocarbon oils. The alcohol or ketone can be any alcohol or ketone having greater than 7 carbons that is sufficiently miscible with oil and sufficiently immiscible with water to form an emulsion with water. Preferably, the alcohol or ketone has a low volatility such that it does not boil off to any significant extent during the forming and extracting processing steps. Also, it is desirable if it does not air oxidize to any significant extent. If desired, the alcohol or ketone can be substituted with a sulfoxide, for example, or any compound that has at least one hydrophilic end and that suppresses the surface tension of the water. A preferred forming/extracting medium contains peanut oil and oleyl alcohol, which are combined in a volumetric ratio of about 1:1 and used at a temperature of about 80–100° C. Peanut oil has a high viscosity and nonpolarity while oleyl alcohol adds extractive properties to the medium. Mixtures of the two allow viscosity, nonpolarity, and extraction capacity of the medium to be controlled. Depending upon the ratio of sol to forming medium, extraction times of about 1 minute to 4 hours can be used to fully gel the zirconia spherules.

In the fed batch oil emulsion process ("FBOM"), the emulsion is completely formed prior to extraction and gelation and the aqueous zirconia sol is concentrated. Concentration of the aqueous zirconia sol before it is used to form an emulsion increases the stability of the emulsion. This eliminates the need for continuously reforming the emulsion with high speed rotary mixers as extraction and gelation occur. It also allows for an increase in batch size without a scaled increase in the amount of associated water that needs to be extracted. A nonionic surfactant can be added to the sol to help control the final particle sizes as with the SOM method. Emulsion formation occurs by mixing the sol and a forming medium in an in-line mixer. The forming medium is a nonpolar liquid or mixture of liquids that will form an emulsion with the polar sol. Optionally, it may have some polar character as long as it is still capable of forming a two phase emulsion with the sol. The emulsion is transferred to an extraction medium where the emulsion is maintained while all or a portion of the water is removed with heating and stirring. The extraction medium is a liquid with sufficient polar character to extract water from the sol droplets and sufficient nonpolar character to maintain the two phase emulsion created with the in-line mixer. Often, the extracting medium is also used as the forming medium, although the two steps are separate in the FBOM process. The drying results in gelled, solid spherules that consist of aggregated colloid particles that can be conveniently separated from the medium by any suitable method, e.g., filtration.

The FBOM forming medium can contain an oil, alcohol, ketone, or any of the materials described above for the SOM forming/extracting medium. Preferably, the FBOM forming medium contains at least an oil, alcohol, ketone, or mixture thereof, with carbon or silicon backbones having about 12–24 units. Such preferred materials have the appropriate viscosity, nonpolarity, and chemical stability for the oil emulsion process. Examples include vegetable oils such as peanut oil, safflower oil, corn oil, canola oil, sunflower oil, as well as mineral oils, silicone oils, and hydrocarbon oils such as 12–24 unit linear and branched alkanes. The FBOM extracting medium can contain an alcohol, ketone, or sulfoxide, or any of the materials described above for the SOM forming/extracting medium. Preferably, the FBOM extracting medium contains at least an alcohol, ketone, sulfoxide, or mixture thereof, with carbon backbones having about 8–24 carbons. These liquids have the appropriate nonpolarity, viscosity, nonvolatility, chemical stability, and water extraction capacities to maintain the two phase emulsion while extracting water. Examples include, but are not limited to, octanol, decanol, octyl ketone, decyl ketone, octyl sulfoxide, and oleyl alcohol. The forming and extracting media can be the same liquid or mixture of liquids, e.g., peanut oil and oleyl alcohol, although this is not a requirement.

Referring to the schematic in FIG. 2, the FBOM process can be described as follows. A forming medium 3 and a concentrated sol 2 (layered with additional forming medium 1 on top) are each pumped with peristaltic pumps 4 and 5 to a "Y" 6 where the streams are combined. The combined stream then passes through an in-line mixer 8 where the emulsion 9 is formed. The in-line mixer is shown with a turn 7 in it. Although this is not required, it is preferred to enhance mixing of the concentrated sol 2 and the forming medium 3. From the in-line mixer 8, the emulsion 9 is sent to the batch vessel 10. The batch vessel 10 is filled with an extracting medium 12, which is heated with the heating bath 13 and mixed with a batch mixing impeller 15, which is attached to motor 16. The heating bath 13 can be filled with water or a higher temperature heating fluid 17. It is preferably insulated with a porous material 18 to achieve consistent heat transfer to the batch vessel 10 and extracting medium 12. After all the concentrated sol 2 has been transferred to the batch vessel 10, the pumping is continued to pump the forming medium 1 through the lines to clear the in-line mixer of the concentrated sol 2. Mixing and heating in the batch vessel is continued to eliminate water from the droplets. When sufficient water has been eliminated, the droplets form solid spherules consisting of aggregated colloid. Stability is tested by simulating the wash protocol on small samples from the batch and observing them under a light microscope. The spherules are collected and washed after they are judged to be sufficiently stable.

Processing parameters, such as sol composition and pH, colloid size, medium composition, temperature of medium, and time of drying, for example, are necessary to control for consistent particle formation using either the SOM process or the FBOM process. For example, rotary mixing rates for the SOM process, and flow rates through the in-line mixer for the FBOM process control the sizes of the final particles. Although the particles used in the fluidized bed systems described above include a zirconium oxide core, the methods of the present invention can be adapted to use other inorganic colloidal particles. That is, although the expanded bed adsorbent material described above includes surface-modified zirconium oxide particles, the methods described above can be used to make other ceramic particles.

Thus, the inorganic colloidal particles used in the oil emulsion processes, i.e., SOM or FBOM, can be made of metals, metal oxides, metalloid oxides, as well as metal or metalloid oxide precursors (such as hydroxides that can be converted to oxides at elevated temperatures) having one or more of their dimensions within a range of about 1 nm to about 1 $\mu$m. These colloidal particles must also preferably be capable of forming a stable sol. As used herein, a "stable-sol" is a solid-in-liquid two phase system wherein the solid consists of colloidal particles that do not begin to settle out of, or separate from, the liquid upon standing for about 2 hours (by visual inspection). Typically, this occurs if the inorganic particles are generally water insoluble and generally acid insoluble at a pH of about 2. Preferably, the particles have surface hydroxyl groups that assist in dispersing the colloidal particles.

Suitable sources of inorganic oxides are also refractory, i.e., they do not melt or otherwise decompose (other than to convert to an oxide if in the form of an oxide precursor, such as a hydroxide) at elevated temperatures. Preferably, they do not melt or otherwise decompose at temperatures up to about 500° C., and more preferably up to about 1000° C. Typically, suitable refractory particles have melting points greater than 1000° C. Lower melting oxides, or hydroxides that are converted to oxides by heating, can be used if the organic polymer constituent of the aggregate is removed by slow oxidation of the organic polymer at lower temperatures.

By definition, colloidal particles have at least one of their dimensions within a range of about 1 nm to about 1 $\mu$m. Preferably, no dimension is larger than about 1 $\mu$m. Particles having any dimension larger than about 1 $\mu$m are generally not suitable for use in preparing the desired spherical particles of the present invention. Typically, irregularly shaped, nonuniform, large particles form from such colloidal particles. More preferably, no dimension of the colloidal particles is larger than about 0.5 $\mu$m (5000 Å). Most preferably, the colloidal particles are generally spherical having an average particle size of about 30–150 nm (300–1500 Å).

The size of the colloidal particles contribute to the final pore size of the resultant sintered particles. Thus, it is particularly desirable for the samples of colloidal inorganic particles used to be generally uniform in size. By this, it is meant that at least about 70% of the colloidal particles in a sample are within a range that spans ±50% of the average particle size of the colloidal particles.

Preferably, the inorganic colloidal particles include the metals in Groups IIIB, IVB, VB, and VIB, the metals and metalloids in Groups IIIA, IVA, and VA of the Periodic Table, as well as the lanthanides. In this context, metalloids and oxides or hydroxides of metalloids such as silicon, aluminum, and germanium, as well as metals and oxides or hydroxides of metals such as zirconium and tin, are included within the scope of the term "inorganic particle" as long as the particles are colloidal and can form a stable sol in water, preferably acidic water. If the inorganic particles, e.g., the oxides or the hydroxides that convert to oxides, are somewhat soluble in acid, they can be coated with an impervious layer of a less soluble inorganic oxide, such as silica, for example. Of these preferred inorganic particles, inorganic oxide particles, e.g., metal oxides and metalloid oxides, are the more preferred. Most preferably, the colloidal inorganic particles are alumina ($Al_2O_3$), titania ($TiO_2$), as well as silica ($SiO_2$) and zirconia ($ZrO_2$) or both ($ZrSiO_4$). Again, although these colloidal particles can be used in the oil emulsion methods of the present invention, only zirconium-based colloids are used in the preparation of particles for use in fluidized bed systems and methods for the separation of proteins.

In particularly preferred applications, the colloidal particles are zirconium oxide ($ZrO_2$). Colloidal dispersions of zirconium oxide suitable for use as the $ZrO_2$ source used to prepare the sintered particles of the present invention are manufactured by Nyacol Inc., Ashland, Mass. These dispersions contain about 20 wt-% $ZrO_2$, wherein the colloidal $ZrO_2$ particles vary in average diameter, e.g., from about 10–250 nm. For example, Nyacol Zr 100/20 is an aqueous dispersion containing 20 wt-% colloidal $ZrO_2$ particles, the majority of which are about 100 nm in diameter.

Minor amounts of noncolloidal sources of the desired inorganic particles can be included within the sols used in the methods of the present invention. For example, noncolloidal $ZrO_2$ sources, i.e., those that do not produce a stable sol as defined above, can be included along with the colloidal $ZrO_2$ particles used to prepare the spherules of the present invention. Thus, chloride, nitrate, sulphate, acetate, formate or other inorganic or organic salts of zirconium, such as the oxysalts and alkoxides, can be included with the $ZrO_2$ sol and the mixture used to make the final sintered polymer-free aggregates. In such mixtures, however, colloidal $ZrO_2$ particles make up a major part of the total $ZrO_2$ present.

The final sintered particles that contain a metal oxide, e.g., $ZrO_2$, can also include a minor amount (preferably less than about 20 mole-%) of a secondary metal oxide. For example, other metal oxides (or precursors thereof) can be included in the sols of the desired metal oxide (or precursor thereof), e.g., $ZrO_2$, so as to stabilize a particular crystalline phase of the desired metal oxide or to retard grain growth in the sintered particles. For example, salts or oxides sols of metals such as yttrium, magnesium, calcium, cerium, aluminum, and the like, can be included at levels of up to about 20 mole-% in a sol of $ZrO_2$. $ZrO_2$ particles fired in air or in oxidizing atmospheres that do not contain other oxide additives display either monoclinic, tetragonal, or pseudocubic crystal structures when cooled to room temperature. Higher firing temperatures and longer firing times favor the presence of the monoclinic phase. The inclusion of other metal oxides allows the preparation of particles that possess either monoclinic, tetragonal, or cubic crystalline structures.

The aqueous sol of dispersed inorganic oxide colloidal particles can include a miscible organic solvent capable of lowering the polarity of the liquid in the sol or capable of increasing the volatility of the dispersing phase of colloidal sol to increase drying and gelation rates in the oil emulsion process. Organic solvents having a lower dielectric constant than water can be used as long as they are miscible with water and form a stable sol as defined above. The organic solvent should also be generally noninterfering in the gelling and extracting steps of the oil emulsion process. Suitable such miscible organic solvents include alcohols such as methanol, ethanol, propanol, isopropanol (i.e., 2-propanol), as well as acetonitrile, tetrahydrofuran, dioxane, and dimethylsulfoxide.

Finally, the inorganic particles are sintered to increase their mechanical strength. Sintering may be visualized as the closing of pores within the aggregates due to the surface tension of the solid surface which exerts a contracting force on the colloidal particles surrounding a pore. Since the compressive strength of the aggregates is low at high temperature, the colloidal particles are drawn together and the pores between them shrink. A temperature that reduces the specific surface area of the aggregates by at least about 10% below the value obtained on a powder dried from the original sol is generally sufficient. Preferably, sintering occurs at a temperature of about 750–1000° C., although temperatures above 1000° C. can be used. Sintering is carried out for a time effective to increase the mechanical strength of the particles a desired amount. Typically, about 1–15 hours is preferred. Sintering can be carried out in an oxygen atmosphere, although this is not necessary.

Objects and advantages of this invention are further illustrated by the following examples. The particular materials and amounts thereof recited in these examples as well as other conditions and details, should not be construed to unduly limit this invention. All materials are commercially available except where stated or otherwise made apparent. All percentages are by weight unless otherwise specified.

Experimental Examples
I. METHODS
A. Synthesis of Porous Zirconium Oxide Particles Using the SOM Process Porous zirconia particles were synthesized using an oil emulsion process in the presence of surfactant (SOM). One thousand angstrom zirconium oxide colloid (Nyacol Lot IV-40) was centrifuged for two hours at 1,590×g (3,000 rpm, Beckman JA 10 rotor) to select the larger granules. Batches of 80 g of colloid were resuspended by shaking in nitric acid, pH 3, to obtain a colloidal sol of approximately 16% (wt/wt). One thousand two hundred ml of peanut oil (Baker's Secret) and 1,200 ml of oleyl alcohol Eastern Chemical) were poured together to form the forming extracting medium, agitated using two 3-blade propellers (45° pitch) at 450 rpm (lower propeller 10.5 cm diameter; upper propeller 7.6 cm diameter; bottom propeller 2 cm above the bottom of the beaker; top propeller 5 cm above bottom propeller) and concurrently preheated to 85° C. in a 18.3 cm diameter 4-liter polypropylene beaker in a boiling water bath. Forty grams of urea and 0.33 ml of non-ionic surfactant (TRITON™ X-100, available from Sigma Chemical, St. Louis, Mo.) per 80 g of colloid were dissolved in the resuspended sol. The mixture was then poured into the agitated, preheated oil and alcohol mixture with constant stirring to create the sol/oil emulsion. The mixture was heated and stirred for 4 hours in order to eliminate water from the sol droplets so that they would form solid aggregates. During the drying process, the droplets densified, the colloid granules within the droplets began to flocculate, and ultimately, the droplets solidified into stable, intact particles containing totally aggregated colloid with little water. During drying, particle size and stability were monitored using light microscopy (230× magnification). When coalescence was no longer observed and when split particles began to be observed, the agitation rate was reduced to 360 rpm. After 4 hours, drying was complete and the bath was removed from the heat. The particles were settled for 5 minutes before the oil/alcohol mixture was decanted to remove the smallest particles. The remaining particles were washed 3 times with 75–100 ml of hexane, three times with 25–50 ml of isopropyl alcohol, and dried using vacuum filtration, after which the particles were free-flowing.

Particles were sintered using a programmed temperature oven (NEY) for 2 hours at 375° C., 6 hours at 750° C., and 3 hours at 900° C. A 40° C./minute temperature ramp was used to reach each temperature.

After cooling, free-flowing particles were acid and base treated to establish a consistent surface chemistry. The particles were washed first with carbonate-free, double-distilled water with sonication (Bransonic® Ultrasonic Cleaner Model 1200) under vacuum for 15 minutes. The liquid was decanted and the particles washed and gently rocked in excess 0.5 M carbonate-free NaOH on a shaker table overnight. The supernatant was decanted, the particles rinsed with carbonate-free, double-distilled water and the supernatant decanted. The particles were then washed with gentle rocking in excess 0.5 M carbonate-free nitric acid on a shaker overnight, the supernatant decanted, and rinsed with copious amounts of carbonate-free, double-distilled $H_2O$ and dried under vacuum at 100° C. for 8 hours. The particles were then sonicated in carbonate-free, double-distilled $H_2O$ under vacuum and stored in carbonate-free, double-distilled $H_2O$ until classification.

Particles were classified to achieve an average particle size of 50 $\mu$m by settling prior to elutriation (i.e., classification by flowing liquid). Settling was carried out in double-distilled $H_2O$ in a graduated cylinder (1 liter) followed by decanting the fumes from the top. Elutriation was done with ascending fluidization either in a 30 cm×1 cm (inside diameter, "id") (Ace Glass Co.) or a 15 cm×2.5 cm id (Kontes) glass column at a flow rate sufficient for 3- to 4-fold expansion of the original settled bed volume for at least 30 minutes. Column height was adjustable with a hydraulic plunger positioned at least 1 centimeter above the expanded bed height. During elutriation, fines left the column and the top of the bed was not well defined. Following elutriation, particles were settled overnight and then the bed was progressively expanded. Any remaining small particles eluted until a stable expansion was achieved for at least 10 minutes after 2-, 2.5-, and 3-fold expansion from the settled bed height. A stable bed expansion is defined as one in which there is no visible bed "boiling" wherein the surface is disrupted, no fluid jetting wherein there are no streams of high velocity liquid, and no fines being eluted from the top of the bed. Bed height was determined using a transparent scale attached to the outside of the column. Particles were later removed from the column following BSA adsorption experiments and air dried for determination of particle size distribution.

Particles were characterized by determination of mean diameter and particle size distribution by both screening (Small Parts, Inc., Miami Lakes, Fla.) and electronic particle size distribution (Coulter LS100) methods. Particle surface area and pore volume were determined by nitrogen BET adsorption and desorption using a PSI porosimeter (Micrometrics ASAP 2000 V3.00), as described by S. Brunauer et al., *J. Am. Chem. Soc.*, 60, 309 (1938), and S. J. Gregg et al., *Adsorption Surface and Porosity*, Academic Press, New York (1982). Particle specific gravity (i.e., the effective particle density during fluidization) was calculated from measurements of apparent density and from nitrogen porisimetry data. Apparent density was determined by packing dry particles into a 5.00 ml volumetric flask by successive filling and tapping until the particles were completely packed. The effective density was calculated from the apparent density by assuming a void fraction of 0.36 in the volumetric flask. Effective particle density was also calculated from nitrogen porisimetry data by assuming that the volume of $N_2$ adsorbed/g $ZrO_2$=particle void volume/g $ZrO_2$. Both calculations were based on a specific gravity of 5.7±0.1 g/cm$^3$ for monoclinic $ZrO_2$. These methods for particle density determination were compared with the observed particle density during fluidization. Particle morphology was examined using a scanning electron microscope (SEM, Hitachi 5-450). Viewing samples were prepared using Au/Pd sputtering at 15 $\mu$A in argon at 50 $\mu$m Hg pressure for 3 minutes.

B. Synthesis of Porous Zirconium Oxide Particles Using the FBOM Process

The Fed Batch Oil Emulsion (FBOM) process consisted of the following five steps. In the first step, a zirconia/nitric acid sol (Nyacol Lot IV-40, 20%, 1000 Å, pH 3) was concentrated to 44.5% by centrifugation and resuspension. The sol was centrifuged for two hours at 1,590×g (3,000 rpm, Beckman JA 10 rotor) and 0° C. The supernatant was collected and divided into six 500-ml centrifuge bottles and centrifuged for two hours at 17,700×g (10,000 rpm, Beckman JA10 rotor) and 0° C. The six pellets were then resuspended in an amount of pH 3 nitric acid needed to end up with slightly more than 44.5% zirconia at the end of the concentration process. This averaged about 38 g per centrifuge bottle or about 228 g total. The resuspension was done using a 37° C. shaker oscillating at 240 rpm for 12 to 24 hours. A third centrifugation was done for 5 minutes at 17,700×g and 0° C. to pellet out aggregated colloid particles. The pellet was discarded. The density of the final supernatent was then measured to determine its weight percent zirconia. An amount of the original sol was added to bring its final concentration down to 44.5% zirconia.

Concentration was done for two reasons. First, it allowed the batch size to be increased greatly without an increase in drying time. For example, in the SOM process, 16% sol was used with 80 g of zirconia and 422 g of nitric acid (water) present. At a concentration of 44.5%, if FBOM had 422 g of nitric acid present, it would have 338 g of zirconia. So the batch size could be increased 4.2 times without any increase in drying times. Second, it allowed larger batches to be made with smaller total batch volumes (less oil phase) without adversely affecting the established droplet (particle) size distribution in the batch vessel. Normally, a higher sol-to-oil ratio would mean more collisions between droplets and increased rates of coalescence. But tests using the concentrated sol under the conditions involved in the FBOM process resulted in no observable coalescence, while the unconcentrated sol was observed to readily coalesce under the same conditions. The elimination of coalescence was thought to be due to the higher viscosity and surface tension of the more concentrated sol. With coalescence virtually eliminated, not as much oil phase was needed to separate droplets. This meant that more concentrated batches of particles could be made without adversely affecting the desired particle size distributions.

For the second step, emulsion formation, 800 g of this final concentrated sol (444 g nitric acid, 356 g zirconia) was sent through an in-line mixer along with a forming medium. A two phase emulsion was created using 12 inches of $\frac{3}{16}$ inch outside diameter (od) polyacetal in-line mixers (Cole-Parmer, Niles, Ill.) contained in $\frac{5}{16}$ inch od ($\frac{3}{16}$ inch id) Tygon tubing (Cole-Parmer). A diagram of the apparatus used for this step and for the drying step is shown in FIG. 2. The emulsion consisted of the previously concentrated zirconia colloid sol and the forming medium consisted of peanut oil (Baker's Secret) and oleyl alcohol (Eastern Chemical) mixed in a 1:1 volume ratio. The sol was pumped at a rate of 37.5 ml/minute and the forming medium was pumped at 111 ml/minute. The streams were combined using a glass "Y" (Kimax) and flowed through the in-line mixer at a rate of 148 ml/minute at a 1:3 volume ratio (sol:forming medium). Pumping was accomplished using peristaltic pumps. Temperatures of the sol and forming medium were about 22° C. As the sol and forming medium were pumped through the in-line mixer, an emulsion was created consisting of sol droplets suspended in the forming medium. The size distribution of the sol droplets was such that the final resulting particles would have a fairly narrow size distribution centered around particles with a mean diameter of 50 µm.

As seen in FIG. 2, a 180° turn was put in the in-line mixer to ensure that the total volume passing through the in-line mixer underwent the same shear stresses no matter where it entered the mixer (e.g., near the wall or near the center). With a turn such as this, there is a greater radial exchange of material between the walls and the center of the in-line mixer. All of the sol was able to be completely pumped through the in-line mixer without air bubbles by adding 50 ml of the forming medium to the top of the sol and pumping for an extra minute to clear the lines of sol. In addition, during this minute, the sol line under the glass "Y" was manually held up to allow the more dense sol to pass through this low spot where it would otherwise pool. The total time for emulsion formation lasted about 13.5 minutes plus one minute to clear the lines of sol. During this time, an emulsion with a total of 506.5 ml of sol (800 g) and 1647 ml of forming medium (1609.5 ml through the oil lines, 37.5 ml through the sol lines) was pumped into the batch vessel where the third step, drying and particle formation, occurred.

The heated, uncovered, stirred batch vessel was used to maintain the droplet size distribution while providing the conditions necessary to dry the droplets and form solid, stable particles. This was accomplished by maintaining the emulsion with agitation vigorous enough to keep the higher density droplets suspended and to prevent droplet coalescence but moderate enough to prevent droplet/particle breakage. This was carried out in a 12-inch tall plastic batch vessel with dimensions of 7 inches wide by 10 inches long at its base diverging to 7.5 inches wide by 10.5 inches long at its top. Before the addition of the emulsion, the vessel was filled to 3.5 inches (3000 ml) with the extracting medium, which was the same as the forming medium (1:1 volume ratio of peanut oil to oleyl alcohol). This was agitated with a centered, 5-inch diameter, 5-bladed impeller (Jiffler brand available from Knox Lumber Co.) rotating at 295 rpm under the power of an electric mixing motor (BDC 3030, Caframo, available from Baxter Diagnostics, Inc., Scientific Products Division, McGraw Park, Ill.) while it was preheated to 95° C. using a boiling hot water bath insulated with foam.

When the temperature reached 95° C., the pumps were started to create the emulsion. For the 14.5 minutes the emulsion flowed into the heated, agitated batch vessel, the batch temperature dropped to 76° C. from 95° C. and the batch depth increased to 5.15 inches. As the depth increased, the agitation rate was increased without the development of vortices, which cause air bubbles to be whipped into the batch. Vortices were avoided because they can cause problems with particle to particle consistency. The agitation rate was increased gradually to a final value of 372 rpm from 295 rpm over a time period of about 7 to 8 minutes.

The batch emulsion was continually heated with the boiling hot water bath and stirred at 372 rpm for a total of 90.5 minutes in order to eliminate the water from the sol droplets. The overall drying rate during this time was equal to the mass of nitric acid at the start, minus the mass of nitric acid at the end, all divided by the total drying time. There were 444 g of nitric acid at the start. The drying process took 90.5 minutes. Estimating from the final calculated void fraction, there were (0.565 ml water/0.435 ml zirconia)(1 ml zirconia/5.7 g zirconia)(356 g zirconia)=81 g (about 81 ml) of nitric acid at the end of the drying process. So the drying rate was about 4.0 g/minute. Dividing by the amount of zirconia present, the drying rate per mass of zirconia was about 1.1 g water/g zirconia/minute. As the water from the emulsion was eliminated, the sol droplets densified, the colloid granules within the droplets began to flocculate, and ultimately, the droplets solidified into stable, intact spherules containing totally aggregated colloid with little water present (estimate 356 g zirconia/(356 g+81 g water)=81% zirconia).

The status of the droplets/particles was monitored periodically during the drying process by examining samples under a 230× light microscope. Size, approximate density, coalescence, and stability of the droplets/particles could be readily observed. In addition, stability was also tested by simulating the wash protocol on a small sample and examining it under the microscope. The particles were considered stable to the solvent wash when the largest particles would survive the wash and subsequent placement under a cover slip on a microscope slide. The particles were sufficiently stable to undergo collection and washing 90.5 minutes after the start of emulsion formation.

When the droplets formed solid, stable particles, they were collected and washed in the fourth step of the process using vacuum filtration and isopropanol. The particles were collected and washed in order to separate them from themselves and from residual oil and water. This was done by the following procedure. After the particles were judged sufficiently stable, the agitation was turned off and the batch was allowed to sit for about 10 minutes. Even though almost all of the useful particles (i.e., those with a particle size of at least 38 µm) settled out of the oil phase in this time, the smaller particles still in the oil phase were collected in order to get a more accurate representation of the size distribution of all the particles. The oil and small particles were filtered under vacuum with fast flow filter paper lining a 10.5 cm Buchner funnel. Three filter papers were used to filter about 1600 ml of oil each time. The filter papers were then set aside.

The particle cake left behind in the batch vessel was then resuspended in isopropanol, small portions at a time (200 ml of isopropanol was used to resuspend about ⅕ of the particles). The suspended particles were poured into the same Buchner funnel under vacuum but lined with a new sheet of fast flow filter paper. The above two steps were repeated 5 times until all of the particles had been transferred to the funnel. The residue of particles from the batch vessel and the small particles on the three previous filter papers were also rinsed into the funnel using a total of about 600 ml of isopropanol.

After the isopropanol coming out of the bottom of the funnel slowed to a drip, the particles were rinsed with 200 ml of isopropanol. This step was repeated twice, waiting for the isopropanol to slow to a drip before repeating. The total isopropanol used to wash the particles was about 2.2 liters. The particles were then completely dried under vacuum.

Finally, in the fifth step of the process, the particles were sintered at high temperature to remove residual organic impurities, eliminate micropores, and provide strength by increasing intercolloidal bonding. The particles were transferred to a porcelain crucible large enough so that the depth of particles was no more than 2.5 cm. Using a programmed temperature oven (NEC), the particles were heated for 2 hours at 375° C. to burn organics, for 6 hours at 750° C. to burn off carbon and nitrogen, and for 3 hours at 900° C. to sinter the colloid bonds. A 40° C./minute temperature ramp was used to reach each temperature. The particles were characterized in the same way the SOM particles were to determine particle size distribution, particle surface area, pore volume, apparent density, effective density, and morphology. Before use, the particles were acid and base treated to establish a consistent surface chemistry, and classified with elutriation, as with the particles generated by the SOM process.

C. Expanded Bed Methods

Fluidization and protein adsorption studies were carried out in a 2.5×15 cm glass column (Kontes) with a hydraulic adjustable Teflon plunger and Teflon end fittings. The plunger was equipped with either polymeric frit or stainless steel screen (38 µm) on the end exposed to the particle bed. Both sintered stainless steel frit and 8 micron, twilled dutch weave, stainless steel screens (Small Parts, Inc.) were evaluated for inlet flow distributors. Inlet screens were attached to a modified 45° flow distribution system (FIG. 1) or a modified column end fitting which has a shallow 4° cone. The screen was secured to the end fitting with either a flat neoprene binder ring and a thin O-ring (FIG. 1A) or with a Teflon sealing ring (FIG. 1B). The stainless steel screen was replaced with a new screen after every third experiment. The fluidized bed was connected to a peristaltic pump (Buchler or Cole Parmer) using 0.8 mm id Teflon tubing and tube fittings (Chrom Tech). Either Tygon or Cflex tubing was used in the peristaltic pump. A 316 stainless steel pressure gauge (ABM) was attached via a three-way connector between the pump and the column inlet. Protein effluent absorbance was measured at $280_{nm}$ using a UV detector (Pharmacia UV-MII) and the signal recorded on a chart recorder (Linseis L6012). Flow rates were measured with a glass graduated cylinder and a stopwatch. Column height to diameter ratio was 2.1–2.3 cm to 2.5 cm.

D. Determination of Flow Hydrodynamics

Residence time distribution ("RTD") studies were performed using a tracer stimulus method, as described in N. M. Draeger et al., *Trans. Int. Chem. Eng.*, 69, 45 (1991), and Wnukowski and A. Lindgren, *Recovery of Biological Products IV*, Engineering Foundation Conference, Interlaken (1992), to assess the degree of dispersion in the liquid phase in relation to column inlet geometry and fluidization velocity. $NaNO_2$ (0.5 ml of 1 M) in 100 mM NaF, 50 mM MES buffer (pH adjusted to 5.5 with 5 M KOH) was injected into the flow system using a 0.8 mm id Teflon multiport sample injection valve (Rheodyne model 5020, Chrom Tech, Apple Valley, Minn.) placed between the fluid reservoir and the pump. The UV absorbance of $NO_2^-$ in the column effluent was measured at $254_{nm}$ using a flow cell detector with a total cell volume of 30 µl (UV-M II Monitor, Pharmacia LKB Biotechnology, Piscataway, N.J.). Peak data were recorded every 0.1 second using a Data Acquisition software (Rainin, Woburn, Mass.).

The relative degree of mixing in the liquid phase was measured for the entire system (tubing, fittings, bed, particles, detector) as well as the system tubing alone with the column bypassed by connecting the column inlet directly to the column outlet. System dispersion as a function of column inlet flow geometry was measured without particles in the column by resting the hydraulic plunger on top of the teflon ring (see FIG. 1B) with the screen in place. Two inlet flow geometries were studied as a function of bed expansion: the 4° shallow cone and a 45° cone (FIG. 1).

The tracer, $NaNO_2$, was shown not to interact with the zirconia surface in the presence of fluoride by comparing the retention time of repeated injections of 1 M $NaNO_2$ at 100 mM and 200 mM NaF. The retention time was equal at both NaF concentrations. For bed expansion RTD measurements, the particle bed was first expanded to the appropriate height and allowed to stabilize for approximately 5 minutes before tracer injection.

The zeroth moment, peak asymmetry, and peak area/maximum peak height were calculated for each tracer effluent peak. The zeroth moment was calculated as: $m_o = Q^* \Delta t^* \Sigma C_i$, where Q is the volumetric flow rate (ml/minute), $\Delta t$ is the data acquisition time interval (minutes), and $C_i$ is the UV monitor voltage output (µV). The summation limits were 3% of the maximum peak height. Peak asymmetry was measured at 50 percent of maximum peak height and calculated as: (c–b)/(b–a), where b is the time of tracer peak maximum, (c–b) is the time length of the peak tail, and (b–a) is the time of the length of the peak front.

E. Determination of Dynamic Binding Capacity

Bovine serum albumin (BSA) was used as a model protein in order to determine protein adsorption during fluidization and to compare the characteristics of fluoride-modified zirconium oxide particles with previous studies of BSA adsorption using fluidized, polymeric ion-exchange adsorbents. The surface of bare zirconia particles was modified by adsorption of fluoride from the mobile phase loading buffer (50 mM MES, 100 mM NaF, pH 5.5), which is described by J. A. Blackwell et al., *J. Chromatogr.*, 549, 59 (1991). Adsorbed fluoride was stripped during column washing with 0.25 M NaOH but the surface could be regenerated by washing the column with fluoride buffer. BSA was adsorbed onto the fluoride-modified zirconium oxide particles from a loading concentration, $C_o$, of 4 mg/ml. BSA was eluted by a step increase in ionic strength using an elution buffer consisting of 50 mM MES, 100 mM NaF and 750 mM $Na_2SO_4$, pH 5.5, which is described by J. A. Blackwell et al., *J. Chromatogr.*, 549, 59 (1991).

Each BSA breakthrough procedure consisted of first washing with approximately 100 ml of 0.1–0.25 M NaOH, equilibration with loading buffer until the pH returned to within 0.2 pH units of pH 5.5, followed by BSA loading, washing with loading buffer, eluting adsorbed BSA with elution buffer, cleaning with 0.25 M NaOH, and rinsing with double-distilled $H_2O$ until the effluent pH was within 0.5 pH units of that of distilled $H_2O$. Before each adsorption experiment, the particles were gently agitated and allowed to settle for even distribution, the column was checked for vertical orientation, and the plunger lowered to one centimeter above where the height of the expanded bed would be.

For packed bed experiments at constant linear velocity, the plunger was positioned on top of the settled bed. All solutions were filtered through a 0.45 µm filter (Gelman brand filter). All solutions except the loading solution which included BSA were degassed by stirring under vacuum for several minutes. BSA solutions were either made fresh at the start of each experiment or stored at 4° C. for at most several days prior to use. Protein adsorption breakthrough profiles were generated either by protein loading while gradually increasing the flow rate and expanding the bed to its final porosity over a period of 2–2.5 minutes (FIG. 9), or protein loading following prior establishment of a stable fully expanded bed.

Dynamic binding capacity (DBC) was calculated from BSA UV adsorption breakthrough curves recorded on a chart recorder and photographically enlarged to twice the original size (in order to more accurately determine UV absorbance as a function of time) by multiplying the inlet concentration of the loading solution, $C_o$, by the product of the average volumetric flow rate, Q, and the time since the start of loading divided by the settled bed volume. Settled bed volume was determined from the observed bed height, H, and the column inner radius. The DBC was also calculated using the graphical method of C. J. Geankoplis, *Transport Processes and Unit Operations*, p. 700, Prentice Hall, New York, (1993), by the product of the area above the breakthrough curve up to the breakthrough point and ($C_o$) (Q)/(H). Dynamic binding capacity was calculated at $C/C_o$= 0.01 (1% of BSA feed concentration) and 0.05 (5% of BSA feed concentration) in mg BSA loaded per ml of settled bed. Total bed capacity was calculated as the product of the total area above the curve with ($C_o$)(Q)/(H).

F. Bed Cleaning

Particles were routinely cleaned of adsorbed protein using 0.1 or 0.25 M NaOH during bed expansion by flushing with at least 100 ml of base. More vigorous cleaning of the particles was achieved by removing them from the column into a polypropylene flask with 250 ml 0.5 M NaOH with shaking at 300 rpm at 50° C. for 64 hours. Between adsorption experiments, the settled particle bed was saturated with double-distilled $H_2O$ or equilibration buffer.

G. Preparation of Dextran-Coated Zirconia Particles

The dextran (9300 MW) and the iodoacetic acid were obtained from Sigma Chemical Co. (St Louis, Mo.). Boron trifluoride diethyl etherate and 1,4-butanediol diglycidyl ether (BUDGE) were obtained from Aldrich Chemical Co. (Milwaukee, Wis.). All water was deionized and then passed through Barnstead ion Exchange and Organic Free cartridges followed by a 0.45 $\mu$m filter. All water was also boiled for 15 minutes to remove carbon dioxide.

Ten grams of dextran was dissolved in 40 ml of water and then cooled to 0–4° C. using an ice bath. A freshly made 12.5 M sodium hydroxide solution (40 ml) was then added. The solution was then stirred at 4° C. for 30 minutes. Iodoacetic acid (10.5 g) was added gradually over 10 minutes. After all of the iodoacetic acid had been added, the solution was stirred for 10 minutes at 4° C. for 10 minutes. The temperature was then increased to 60° C. and the solution was stirred for 30 minutes. The solution gradually became darker yellow as the reaction proceeded. The solution was then cooled in an ice bath. The pH was reduced to 9 with concentrated HCl. Methanol was then added to the solution gradually while stirring to precipitate the carboxymethyl dextran (CMD). The stirrer was turned off when the white precipitate stopped forming. After the precipitate settled to the bottom, the supernatant was decanted. The precipitate was then redissolved in water and reprecipitated using methanol. The twice precipitated CMD had a slight yellow color, probably due to residual iodine. The substitution of carboxylic groups was determined by using the assay of Horikawa and Tanimura as disclosed in T. Horikawa et al., *Anal. Lett.*, 15, 1629 (1982). Acetic acid was used for the calibration curves. The average percent substitution was 5.1%, or about 3 carboxymethyl groups per chain (57 glucose monomers in a 9300 MW dextran chain).

The coating method is based. on that of X. Santarelli et al., *J. Chromatogr.*, 443, 55, (1988). Carboxymethylated dextran (CMD) (0.1 g) (MW 9300, 5% substitution) was dissolved in 50 ml of 100 mM PIPES (piperazine-N,N'-bis[2-ethanesulfonic acid]), pH 6.5 to make a 2 g/l solution of CMD. To 40 ml of this solution, 4 g of zirconia particles were added. This suspension was sonicated under vacuum for five minutes and then capped. The bottle was then placed on a shaker bath for 2 days, with periodic manual shaking.

After the allotted time, the particles were allowed to settle and the supernatant was decanted. Ethanol (40 ml) was then added and the slurry was shaken for 10 minutes. The particles were allowed to settle for 30 minutes and the ethanol was removed by suction. This procedure was repeated for 50:50 ethanol:chloroform (vol:vol) and chloroform. The particles were then allowed to air dry at room temperature.

The coated particles were placed in a 30 ml septum flask and 10 mL of chloroform were added. The flask was capped and sonicated for 5 minutes. 1,4-Butanediol diglycidyl ether (BUDGE, 17 $\mu$l) was added and the flask was sealed while nitrogen was blown over the top. In a separate septum flask, 7 mi of chloroform was added and sealed. Boron trifluoride etherate (0.5 ml) was then added by syringe. This solution (0.5 ml) was then added to the flask containing the coated particles. The particle suspension was swirled and then allowed to sit for 30–40 minutes. After this time, the solution was removed and the particles were rinsed with ethanol.

H. Modification of Dextran Coating with a Dye

The protocol for carrying out the Cibacron-Blue coupling reaction is described in Bohme et al., *J. Chromat.*, 69, 209 (1972). The scale was reduced to one-third. A quantity of 0.67 g of Cibacron-Blue was dissolved in 20 ml of double-distilled water. Previously dried dextran-coated zirconia particles (3.2 g) were suspended in 120 ml of double-distilled water. The particles were sonicated under vacuum for 15 minutes to remove gases from the particle pores. The Cibacron-Blue solution was then added to the particle suspension and stirred at 60° C. After 30 minutes, 15 g of NaCl was added and the mixture was stirred for 3 hours at 75° C. This was then cooled, washed with copious amounts of double-distilled water, and dried in a 100° C. vacuum oven.

I. Modification of Dextran Coating with a Thiophilic Ligand

Synthesis of thiophilic, affinity-phase coatings of porous zirconia particles involved reacting divinylsulphone (DVS) with dextran-coated particles followed by an end-capping reaction using, for example, mercaptoethanol (HSEtOH) or mercaptopyridine. Previously dried dextran-coated particles (2.8 g) were mixed with 5.6 ml of 0.5 M $Na_2CO_3$ in a 50 ml Erlenmeyer flask. The particles were sonicated under vacuum for 15 minutes to remove gases from the particle pores. A solution of 1.75 ml DVS and 1.75 ml isopropanol was made and combined with the particle solution. The mixture was then shaken at 200 rpm to react the DVS with the dextran coating. After 23.75 hours, the thio-modified particles were washed first with isopropanol followed by double-distilled water. Washing was done by swirling the particles in copious amounts of solvent, settling the particles, and decanting the liquid.

When clean, the particles were ready for the end-capping. $Na_2CO_3$ 0.1 M, 35 ml) was added to the particles to resusend them followed by 3.5 ml of HSEtOH or mercaptopyridine. This mixture was then shaken at 250 rpm for 6 hours to fully react the ends of the thiophilic coating. The particles were again washed in double-distilled water and were then dried in a 100° C. vacuum oven.

II. RESULTS

A. Characterization of Particles

The average diameter after elutriation of SOM particles, as determined by particle screening, and the average hydraulic pore diameter determined by nitrogen porisimetry, varied slightly from batch to batch (Table I) depending upon the extent of removal of water during synthesis (i.e., how much water was present when the particles were collected and washed). The weight percentage of particles as a function of size was determined for an individual batch ("SOM A") and combined batches ("SOM A & B") by screening. Particles prepared by the SOM synthesis were generally spherical with some particles slightly flattened or indented on one side (FIG. 3A). This variation in particle shape is most likely the result of mixing conditions during particle formation. Particles prepared by the FBOM synthesis were predominantly spherical with very few flattened or indented portions (FIG. 3B). Classification by elutriation eliminated adhering surface zirconia resulting in a smooth porous particle surface.

Determination of the effective particle density from direct apparent density measurements of dry SOM A particles (3.32±0.15 g/cm$^3$) and from nitrogen porisimetry measurements (3.30±0.10 g/cm$^3$) agreed well (Table I) with the determination of particle density by fluidization velocity using the Richardson-Zaki relationship, as disclosed in J. F. Richardson et al., *Trans. Inst. Chem. Eng.*, 32, 35 (1954), despite the fact that this relationship is theoretically for particles of 100 μm or larger.

TABLE I

Characterization of SOM Particles

|  | SOM A | SOM A & B |
|---|---|---|
| Mean Diameter (determined by screening) | 54 μm | 43 μm |
| Apparent Density (gavitimetric) |  |  |
| Apparent Density | 1.803 ± 0.017 g/cm$^3$ | 1.696 ± 0.014 g/cm$^3$ |
| Void Fraction | 0.51 ± 0.03 | 0.54 ± 0.03 |
| Effective Density | 3.32 ± 0.15 g/cm$^3$ | 3.18 ± 0.15 g/cm$^3$ |
| Nitrogen Porisimetry |  |  |
| Surface Area | 21.7 ± 0.2 m$^2$g | 21.5 ± 0.2 m$^2$g |
| Void Volume | 0.183 ± 0.002 cm$^3$/g | 0.196 ± 0.002 cm$^3$/g |
| Hydraulic Pore Diameter (4V/A) | 338 Å | 366 Å |
| BET Adsorption Peak | 516 Å | 580 Å |
| BET Desorption Peaks | 292 Å, 310 Å | 312 Å, 363 Å |
| Void Fraction | 0.51 ± 0.02 | 0.53 ± 0.02 |
| Effective Density | 3.30 ± 0.10 g/cm$^3$ | 3.22 ± 0.09 g/cm$^3$ |

The results of two FBOM batches are summarized in Tables II, III, and IV. Table II, "Comparison of Yields," shows the percent and total yields for the FBOM batches and compares them to the SOM technology. Table III, "Comparison of Analyses," shows the measured and observed characteristics of the FBOM batches and compares them with the SOM technology. Table IV, "Particle Comparison Table," compares the measured characteristics and extent of drying of FBOM and SOM particles. It can be seen from the "Yield" table that much higher yields are obtained with the FBOM process than with the SOM process. A final yield of about 31 to 41% of the zirconia available in the original colloid is obtained in the final FBOM particles. The yield for SOM A was only 6.4%.

TABLE II

Comparison of Yields

|  | FBOM A | FBOM B | SOM A |
|---|---|---|---|
| Mass of zirconia in starting sol | 540 g | 540 g | 517 g |
| Mass of zirconia colloid in concentrated sol after centrifugation, resuspension | 356 g | 356 g | 80 g |
| Yield of zirconia colloid in concentrated sol after centrifugation, resuspension | 66% | 66% | 15% |
| Mass of particles after synthesis, sintering | 330.98 g | 331.16 g | 60 g |
| Yield of particles from concentrated sol | 92.9% | 93.0% | 75% |
| Yield of screened 38–74 μm particles after sintering | 75.1% | 73.0% | 81% |
| Expected yield of base/acid washing and elutriation step | 70–90% | 70–90% | 70% |
| Total Yield | 32–41% | 31–40% | 6.4% |
| Expected total mass available in final form | 173–224 g | 167–218 g | 33 g |
| Number of 3:1 H:D 2.5 cm diameter columns (60 g/column) | 2.8 to 3.7 columns | 2.8 to 3.6 columns | 0.55 columns |

TABLE III

Comparison of Analyses

| Analysis | FBOM A | FBOM B | SOM B |
|---|---|---|---|
| SEM Morphology | Spherical | Spherical | Mixture of "chopped" & spherical |
| Colloid size (Coulter) | 1300 Å | 1220 Å | 1460 Å |
| Colloid size (Stoke's eq.) | 260–860 Å avg. 700 Å | 260–860 Å avg. 700 Å | >860 Å avg. 1200 Å |
| Mean particle diameter after sintering, by screening | 50 μm | 48 μm | 54 μm |
| Nitrogen adsorption peak | 446 Å very narrow | 433 Å very narrow | 516 Å |
| Nitrogen desorption peak | 263 Å very narrow | 265 Å very narrow | 310 Å |
| BET surface area | 28.9 m$^2$/g | 27.9 m$^2$g | 21.7 m$^2$g |
| Single pt. vol of pores | 0.230 cm$^3$/g | 0.224 cm$^3$/g | 0.183 cm$^3$/g |
| Hyd dia of pores (4V/A) | 320 Å | 321 Å | 369 Å |
| Effective water-filled density (N$_2$ data) | 3.03 g/cm$^3$ | 3.07 g/cm$^3$ | 3.30 g/cm$^3$ |
| Apparent density | 1.63 g/cm$^3$ | 1.63 g/cm$^3$ | 1.80 g/cm$^3$ |
| Effective water-filled density (App. density) | 3.10 g/cm$^3$ | 3.10 g/cm$^3$ | 3.32 g/cm$^3$ |
| Particle void fraction (N$_2$ data) | 0.57 | 0.56 | 0.51 |
| Particle void fraction (App. density) | 0.55 | 0.55 | 0.51 |

TABLE IV

Particle Comparison Table

| | SOM A | SOM A & B | SOM B | FBOM A | FBOM B | FBOM C | FBOM D | FBOM E | FBOM F |
|---|---|---|---|---|---|---|---|---|---|
| Colloid size | 1460 Å | 1460 Å | 1460 Å | 1300 Å | 1220 Å | 1460 Å | 1250 Å | 1250 Å | 1460 Å |
| Surface Area | 21.7 m²/g | 21.5 m²g | 22.3 m²/g | 28.9 m²/g | 27.9 m²/g | 24.4 m²/g | 30.5 m²/g | 30.9 m²/g | 26.6 m²/g |
| Void Volume | 0.183 cm³/g | 0.196 cm³/g | 0.204 cm³/g | 0.230 cm³/g | 0.224 cm³/g | 0.221 cm³/g | 0.242 cm³/g | 0.218 cm³/g | 0.210 cm³/g |
| Hyd. dia. of pores (4 V/A) | 338 Å | 366 Å | 366 Å | 320 Å | 321 Å | 363 Å | 317 Å | 282 Å | 317 Å |
| BET Nit Ads Peak | 516 Å | 580 Å | 879 Å | 446 Å | 433 Å | 901 Å | 448 Å | 411 Å | 515 Å |
| BET Nit Des Peak | 310 Å | 312 Å<br>363 Å | 395 Å | 263 Å | 265 Å | 396 Å | 288 Å | 264 Å | 332 Å |
| Void Fraction | 0.51 | 0.53 | 0.54 | 0.57 | 0.56 | 0.56 | 0.58 | 0.55 | 0.54 |
| Eff. Density | 3.30 g/cm³ | 3.22 g/cm³ | 3.19 g/cm³ | 3.03 g/cm³ | 3.07 g/cm³ | 3.08 g/cm³ | 2.98 g/cm³ | 3.10 g/cm³ | 3.14 g/cm³ |

B. Characterization of the Hydrodynamic Behavior of Expanded Beds

The flow behavior of porous SOM particles was characterized in water and in buffer containing BSA. The relationship between bed porosity, $\epsilon$, and superficial liquid velocity, u, were found to fit well to the Richardson-Zaki relationship, $u = u_t \epsilon^n$, as discussed in J. F. Richardson et al., *Trans. Inst. Chem. Eng.*, 32, 35 (1954), with n≈5.55 indicating laminar flow. See, Y. S. Chong et al., *Powder Technology*, 23, 55 (1979); J. F. Richardson et al., *Trans. Chem. E.*, 39, 348 (1961); and L. G. Gibilaro et al., *Chem. Eng Sci.*, 40, 1817 (1985). The terminal velocity, $u_t$, was determined to be 2.7–3.1 mm/second for SOM particles depending upon the particle size distribution of each batch. This observed terminal settling velocity agreed well with the value predicted from the Stokes' equation, on substitution of appropriate values for the physical characteristics for each size of zirconium oxide particles. Protein adsorption studies were carried out with SOM particles whose linear flow velocities were in the range of 100–220 cm/hour (FIG. 4). Settled packed bed (1× bed expansion) studies were carried out at a linear velocity of approximately 100 cm/hour.

The residence time distributions for the tubing system (without particles in the bed) and for the complete system were determined as a function of bed expansion and compared for the standard 4° and conical 45° flow adapters. With SOM particles in the column (packed bed) bimodal peaks were observed using the 4° flow distributor. For this reason, the shallow cone was modified as shown in FIG. 1B which eliminated peak splitting in the tracer pulse signal (FIGS. 5A and 5B).

While the residence time distributions for either flow distribution system at constant flow rate were sharp for the tubing alone and for packed SOM particles, as expected, significant peak broadening was observed as a function of bed expansion for both flow distributors (see FIG. 5B for the 45° inlet flow adapter). Peak broadening was quantified by the ratio of peak area to peak height. Contributing to this observed broadening is the 1 cm dead volume between the expanded bed surface and the column outlet. Peak zeroth moment did not differ significantly between the two flow distribution systems with increasing flow rate either in the absence of particles or for the complete system. In the presence of particles, peak asymmetry increased as a function of flow rate and was greater with the 4° flow distributer. The modified flow distributer shown in FIG. 1A resulted in observable jetting in the column. For these reasons, BSA adsorption studies were carried out using the 45° flow distributor shown in FIG. 1B.

C. Determination of BSA Adsorption and Bed Expansion

BSA desorption was compared between a fixed (settled) and expanded bed of SOM particles (FIG. 6). Adsorption and elution profiles for expanded beds were comparable to the packed bed (FIG. 7). Even though significant peak broadening occurred during adsorption at 2×, 2.5×, and 3× bed expansion, BSA elution by altering the ionic strength at constant flow, and without reversal of flow, was rapid and resulted in a reproducible, sharp elution peak (FIG. 7). This elution method is in contrast to settling of the bed and elution by reversing flow direction which is used for less dense larger expanded bed adsorbents.

DBC varied at constant flow velocity for the packed bed and bed expansion up to 3-fold for SOM particles (FIG. 8) as superficial velocity was increased from 109 to 220 cm/hour (Table V). The two methods used to determine DBC were in good agreement (FIG. 8). An indication of the effect of dispersion in the expanded bed as a function of bed expansion was obtained from the slope of the BSA breakthrough curves at $C/C_o=0.5$, as described in N. M. Draeger et al., *Trans. Int. Chem. Eng.*, 69, 45 (1991), and P. Wnukowski et al., *Recovery of Biological Products IV*, Engineering Foundation Conference, Interlaken (1992).

The method of BSA loading, whether at full expansion prior to loading or while gradually expanding the bed to full expansion during loading, did not significantly affect the DBC. The time to fully expand the bed when switching to BSA loading buffer from equilibration buffer (1.9–2.7 minutes) was approximately one third of the time to 1% BSA breakthrough depending on fluidization velocity (FIG. 9).

The variation in DBC ranged from 54 to 66 mg BSA/ml settled bed depending upon fluidization velocity (Table V) when the bed was expanded to greater than 3-fold. This increase in DBC was unexpected given that mass transfer limitations predict decreasing protein adsorption as bed porosity increases. Table V indicates that comparable BSA binding capacities to much deeper beds of larger DEAE particles with large settled bed height to diameter ratios can be achieved at very high liquid velocities (>100 cm/hour) even with shallow beds of less than 2.5 cm bed height using 43 μm to 54 μm zirconium particles. These zirconia particles allow fluidization at a velocity high enough to reach optimum expansion to minimize dispersion and to allow separation of the adsorbent from entrained solids but with a reduced characteristic diffusion length within the adsorbent compared to currently available technology.

TABLE V

Comparison of BSA Adsorption Characteristics for Porous Zirconium Oxide Particles

| PARTICLES | BED EXPANSION | FLOW RATE (cm/hr) | BED H:D (cm) | DYNAMIC BINDING CAPACITY (mg BSA/ml Settled Bed) | |
|---|---|---|---|---|---|
| | | | | 1% Breakthrough (n) | 5% Breakthrough (n) |
| SOM-A | 1 × | 109 | 2:2.5 | 41 ± 6 (1) | 44 ± 6 (1) |
| | 2.5 × | 164 | | 30 ± 3 (2) | 40 ± 4 (2) |
| | 3 × | 215 | | 41 ± 6 (2) | 47 ± 1 (2) |
| SOM A & B | 1 × | 109 | 2:3:2.5 | 26 ± 2 (3) | 34 ± 2 (3) |
| | 2 × | 110 | | 29 ± 1 (3) | 37 ± 1 (3) |
| | 2.5 × | 158 | | 26 ± 3 (3) | 35 ± 3 (3) |
| | 3 × | 200 | | 28 ± 2 (3) | 35 ± 2 (3) |
| | 3.4 × | 220 | | 29 ± 3 (1) | 33 ± 3 (1) |

Error is ± one standard deviation, n = number of individual determinations

D. Reproducibility of BSA Binding Capacity

Protein adsorption studies using the same column of SOM particles over an eight month period of time revealed several behaviors that resulted in dramatic decreases in BSA DBC. Bed dispersion and DBC were primarily affected by the column inlet flow geometry, since the ratio of column diameter to particle diameter of 500 rendered wall effects insignificant. Similar DBC was obtained using the stainless steel frit or the screen (FIG. 10A), however, the location of the retaining ring on the initial screen design (FIG. 1A) resulted in generation of small fluid jets at the base of the bed which reduced the DBC. Jets were eliminated by altering this design to that shown in FIG. 1B. The frit was more prone to clogging with protein during repetitive adsorption and desorption experiments and could not be adequately cleaned with 0.1 M NaOH. Frit clogging dramatically reduced the DBC from 30±2 mg/ml settled bed volume to 12±5 mg/ml settled bed volume. Insufficient cleaning with 0.1 M NaOH resulted in particle clumping which also reduced DBC more than three fold (FIG. 10B). Clumped particles could be cleaned by stripping with 0.25–0.5 M NaOH with shaking at 50° C. to restore BSA binding capacity to the original level.

E. Performance of Zirconium Oxide Particles After Repeated Cleaning

Repeated cycles of BSA binding, elution and column stripping with NaOH did not result in significant particle fracture, generation of fines (detected as cloudiness at the expanded bed interface), or loss of dynamic binding capacity over a nine month period of SOM particle evaluation. During this time period, the particles were exposed to over 500 column volumes of NaOH both at ambient and at elevated temperatures. Routine storage of the column was feasible at low pH (pH 5.5) without the need for addition of sodium azide. No microbial growth was evident during this time period using low ionic strength fluoride buffer in spite of column storage at ambient temperature. The dynamic binding capacity at a 2-fold bed expansion observed on the initial breakthrough determinations was 30±2 mg/ml settled bed volume. The DBC at the end of eight months of column use with repeated cleaning with NaOH was 32±4 mg/ml settled bed volume. Particle size and size distribution did not appear to be altered as a result of months of repeated adsorption/desorption and base washing cycles.

F. Protein Adsorption at Elevated Temperatures

Repeated cycles of BSA binding at elevated temperatures indicate that DBC increases as temperature increases (FIG. 11). This data was obtained using a column similar to FIG. 1 with a hot water circulation jacket system. Inlet fluids were preheated to the indicated temperature.

By elevating the loading temperature from 25° C. to approximately 45° C., DBC increases by one-third. The column was rapidly eluted, cleaned with base, and reequilibrated at each indicated temperature. In each case, DBC increased with increasing temperatures, and column cleaning became more efficient using strong base at elevated temperatures.

The complete disclosures of all patents and publications cited herein are incorporated by reference as if individually incorporated by reference. While this invention has been described in connection with specific embodiments, it should be understood that it is capable of further modification. The claims are intended to cover those variations which one skilled in the art would recognize as the chemical equivalent of what has been described herein. Thus, various omissions, modifications, and changes to the principles described herein can be made by one skilled in the art without departing from the true scope and spirit of the invention, which is indicated by the following claims.

What is claimed is:

1. An expanded bed system comprising surface-modified zirconium oxide particles having a capacity factor greater than about 10; said particles comprising a core zirconium oxide particle having a particle size of about 30–400 μm and a specific gravity of about 2.5–3.5 g/cm$^3$.

2. The expanded bed system of claim 1 wherein the specific gravity of the core zirconium oxide particle is about 3.0–3.5 g/cm$^3$.

3. The expanded bed system of claim 1 wherein the particle size of the core zirconium oxide particle is about 50–200 μm.

4. The expanded bed system of claim 1 wherein the surface-modified zirconium oxide particles have a capacity factor greater than about 50.

5. The expanded bed system of claim 1, wherein the surface modified zirconium oxide particles have pores.

6. The expanded bed system of claim 5, wherein the pores have a pore size of about 200–1500 Å.

7. The expanded bed system of claim 5, wherein at least about 70% of the pores have a pore size within a range of ±50% of a pore size average of about 200–1500 Å.

8. The expanded bed system of claim 1, wherein the surface-modified zirconium oxide particles comprise a coating of a material selected from the group consisting of a hydrophilic polymer, a carbohydrate polymer having a covalently bound affinity ligand, and a Lewis base.

9. The expanded bed system of claim 8, wherein the hydrophilic polymer comprises polyethyleneimnine.

10. An expanded bed comprising surface-modified zirconium oxide particles having a capacity factor greater than about 10, wherein the surface-modified zirconium oxide particles comprise a core zirconium oxide particle having a particle size of about 30–400 μm and a specific gravity of about 3.0–3.5 g/cm$^3$, wherein the expanded bed has a height to diameter ratio less than about 1:1.

11. An expanded bed comprising surface-modified zirconium oxide particles having a capacity factor greater than about 10, wherein the surface-modified zirconium oxide particles comprise a core zirconium oxide particle having a particle size of about 30–400 μm, a specific gravity of about 2.5–3.5 g/cm$^3$, and an ion-exchange phase comprising fluoride ions.

12. An expanded bed comprising surface-modified zirconium oxide particles having a capacity factor greater than about 10, wherein the surface-modified zirconium oxide particles comprise a core zirconium oxide particle having a particle size of about 30–400 μm, a specific gravity of about 2.5–3.5 g/cm$^3$, and an affinity phase comprising dextran having covalently bound nonprotein affinity ligands.

13. An expanded bed comprising surface-modified zirconium oxide particles having a capacity factor greater than about 10, wherein the surface-modified zirconium oxide particles comprise a core zirconium oxide particle having a particle size of about 30–400 μm, a specific gravity of about 2.5–3.5 g/cm$^3$, and an affinity phase comprising dextran having covalently bound triazine dyes and thiophilic ligands.

* * * * *